United States Patent
Kanovsky

(10) Patent No.: US 10,667,521 B2
(45) Date of Patent: *Jun. 2, 2020

(54) ANTIMICROBIAL MATERIAL COMPRISING SYNERGISTIC COMBINATIONS OF METAL OXIDES

(71) Applicant: ARGAMAN TECHNOLOGIES LTD., Jerusalem (IL)

(72) Inventor: Mechael Kanovsky, Rehovot (IL)

(73) Assignee: ARGAMAN TECHNOLOGIES LTD., Jerusalem (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/703,342

(22) Filed: Dec. 4, 2019

(65) Prior Publication Data

US 2020/0100503 A1 Apr. 2, 2020

Related U.S. Application Data

(63) Continuation of application No. 15/549,018, filed as application No. PCT/IL2015/050142 on Feb. 8, 2015, now Pat. No. 10,537,108.

(51) Int. Cl.
| | |
|---|---|
| *A01N 59/20* | (2006.01) |
| *D06M 11/42* | (2006.01) |
| *C08J 3/22* | (2006.01) |
| *A61K 9/70* | (2006.01) |
| *A61K 33/30* | (2006.01) |
| *A61K 33/38* | (2006.01) |
| *A61K 33/34* | (2006.01) |
| *A01N 25/10* | (2006.01) |
| *A01N 25/26* | (2006.01) |
| *A01N 59/16* | (2006.01) |
| *C08K 3/22* | (2006.01) |
| *D06M 101/04* | (2006.01) |
| *D06M 101/32* | (2006.01) |

(52) U.S. Cl.
CPC ............ *A01N 59/20* (2013.01); *A01N 25/10* (2013.01); *A01N 25/26* (2013.01); *A01N 59/16* (2013.01); *A61K 9/7007* (2013.01); *A61K 33/30* (2013.01); *A61K 33/34* (2013.01); *A61K 33/38* (2013.01); *C08J 3/226* (2013.01); *D06M 11/42* (2013.01); *C08J 2323/12* (2013.01); *C08J 2367/00* (2013.01); *C08J 2491/08* (2013.01); *C08K 3/22* (2013.01); *C08K 2003/2248* (2013.01); *C08K 2003/2286* (2013.01); *D06M 2101/04* (2013.01); *D06M 2101/32* (2013.01)

(58) Field of Classification Search
None
See application file for complete search history.

(56) References Cited

U.S. PATENT DOCUMENTS

| | | | |
|---|---|---|---|
| 2,854,346 | A | 9/1958 | Todd |
| 5,102,726 | A | 4/1992 | Gabbay |
| 5,336,416 | A | 8/1994 | Antelman |
| 5,573,769 | A | 11/1996 | Creech |
| 5,676,977 | A | 10/1997 | Antelman |
| 5,939,340 | A | 8/1999 | Gabbay |
| 5,981,066 | A | 11/1999 | Gabbay |
| 6,124,221 | A | 9/2000 | Gabbay |
| 6,258,385 | B1 | 7/2001 | Antelman |
| 6,436,420 | B1 | 8/2002 | Antelman |
| 6,482,424 | B1 | 11/2002 | Gabbay |
| 6,645,531 | B1 | 11/2003 | Antelman |
| 6,669,966 | B1 | 12/2003 | Antelman |
| 7,169,402 | B2 | 1/2007 | Gabbay |
| 7,296,690 | B2 | 11/2007 | Gabbay |
| 7,364,756 | B2 | 4/2008 | Gabbay |
| 8,173,154 | B2 | 5/2012 | Jung |
| 8,183,167 | B1 | 5/2012 | Delattre |
| 8,512,725 | B2 | 8/2013 | Parsons |
| 9,271,492 | B2 | 3/2016 | Cornmell |
| 9,931,283 | B2 | 4/2018 | Gabbay |
| 9,995,002 | B2 | 6/2018 | Greenwald |
| 2003/0198945 | A1 | 10/2003 | Gabbay |

(Continued)

FOREIGN PATENT DOCUMENTS

| | | |
|---|---|---|
| CN | 103073777 A | 5/2013 |
| EP | 1809306 B1 | 9/2012 |

(Continued)

OTHER PUBLICATIONS

Borkow and Gabbay (2004) Putting copper into action: copper-impregnated products with potent biocidal activities. The FASEB Journal 18(14): 1728-1730.

(Continued)

*Primary Examiner* — Jeffrey T. Palenik

(74) *Attorney, Agent, or Firm* — J.A. Lindeman & Co. PLLC

(57) ABSTRACT

The present invention relates to materials having antimicrobial properties, said materials comprising a polymer having incorporated therein a synergistic combination of at least two metal oxide powders, comprising a mixed oxidation state oxide of a first metal and a single oxidation state oxide of a second metal, the powders being incorporated substantially uniformly within said polymer, wherein the powders have substantially different specific gravities and substantially similar bulk densities and wherein the ions of the metal powders are in ionic contact upon exposure of said material to moisture. There are further provided methods for the preparation of said materials and uses thereof, including in combating or inhibiting the activity of microbes or microorganisms.

11 Claims, 9 Drawing Sheets

(56) References Cited

U.S. PATENT DOCUMENTS

| | | |
|---|---|---|
| 2004/0022868 A1 | 2/2004 | Antelman |
| 2004/0167484 A1 | 8/2004 | Gabbay |
| 2004/0197386 A1 | 10/2004 | Gabbay |
| 2004/0247653 A1 | 12/2004 | Gabbay |
| 2005/0048131 A1 | 3/2005 | Gabbay |
| 2005/0049370 A1 | 3/2005 | Gabbay |
| 2005/0150514 A1 | 7/2005 | Gabbay |
| 2006/0105057 A1 | 5/2006 | Antelman |
| 2006/0127498 A1 | 6/2006 | Sugiura |
| 2007/0184079 A1 | 8/2007 | Gabbay |
| 2008/0152905 A1 | 6/2008 | Hendriks |
| 2008/0193496 A1 | 8/2008 | Gabbay |
| 2008/0241530 A1 | 10/2008 | Gabbay |
| 2008/0311165 A1 | 12/2008 | Gabbay |
| 2009/0010969 A1 | 1/2009 | Gabbay |
| 2012/0321686 A1 | 12/2012 | Bokorny |
| 2013/0195841 A1 | 8/2013 | Gabbay |
| 2014/0065196 A1 | 3/2014 | Gabbay |
| 2014/0271757 A1 | 9/2014 | Agrawal |
| 2015/0038040 A1 | 2/2015 | Gabbay |
| 2015/0044449 A1 | 2/2015 | Foss |
| 2015/0238648 A1 | 8/2015 | Matouk |
| 2018/0028712 A1 | 2/2018 | Kanovsky |

FOREIGN PATENT DOCUMENTS

| | | |
|---|---|---|
| IL | 135487 A | 7/2005 |
| JP | 54151669 A | 11/1979 |
| JP | H03-084066 A | 4/1991 |
| JP | 2003-519188 A | 6/2003 |
| JP | 2009-503019 A | 1/2009 |
| JP | 2011-104809 A | 6/2011 |
| JP | 2013-515679 A | 5/2013 |
| JP | 2015-500819 A | 1/2015 |
| WO | 9806509 A1 | 2/1998 |
| WO | 0181671 A2 | 11/2001 |
| WO | 2004073756 A1 | 9/2004 |
| WO | 2006100665 A2 | 9/2006 |
| WO | 2008029387 A1 | 3/2008 |
| WO | 2010125323 A1 | 11/2010 |
| WO | 2011010221 A1 | 1/2011 |
| WO | 2011051948 A2 | 5/2011 |
| WO | 2013160898 A1 | 10/2013 |
| WO | 2013190317 A1 | 12/2013 |
| WO | 2014030123 A2 | 2/2014 |
| WO | 2014196881 A1 | 12/2014 |

OTHER PUBLICATIONS

Borkow and Gabbay (2005) Copper as a biocidal tool. Current Medicinal Chemistry 12(18): 2163-2175.

Borkow and Gabbay (2005) Endowing textiles with permanent potent biocidal properties by impregnating them with copper oxide. J Text Apparel Technol Manage 5: 1-3.

Borkow and Gabbay (2008) Biocidal textiles can help fight nosocomial infections. Medical HypotheseS 70(5): 990-994.

Borkow and Gabbay (2009) Copper, an ancient remedy returning to fight microbial, fungal and viral infections. Current Chemical Biology 3(3): 272-278.

Borkow et al., (2007) Neutralizing viruses in suspensions by copper oxide-based filters. Antimicrobial Agents and Chemotherapy 51(7): 2605-2607.

Borkow et al., (2008) Could chronic wounds not heal due to too low local copper levels? Medical Hypotheses 70(3): 610-613.

Borkow et al., (2008) Deactivation of human immunodeficiency virus type 1 in medium by copper oxide-containing filters. Antimicrobial Agents and Chemotherapy 52(2): 518-525.

Borkow et al., (2009) Reducing the risk of skin pathologies in diabetics by using copper impregnated socks. Medical Hypotheses 73(6): 883-886.

Borkow et al., (2009) Improvement of facial skin characteristics using copper oxide containing pillowcases: a double-blind, placebo-controlled, parallel, randomized study. International Journal of Cosmetic Science 31(6): 437-443.

Borkow et al., (2010) Copper oxide impregnated wound dressing: biocidal and safety studies. Wounds: A Compendium of Clinical Research and Practice 22(12): 301-310.

Borkow et al., (2010) Molecular mechanisms of enhanced wound healing by copper oxide-impregnated dressings. Wound Repair and Regeneration 18(2): 266-275.

Chen et al., (2013) Preparation of Cu—Ag core—shell particles with their anti-oxidation and antibacterial properties. Current Applied Physics 13(7): 1496-1501.

El-Nahhal et al., (2012) Nanostructured copper oxide-cotton fibers: synthesis, characterization, and applications. International Nano Letters 2(1): 14; 5 pages.

Gabbay et al., (2006) Copper oxide impregnated textiles with potent biocidal activities. Journal of Industrial Textiles 35 (4): 323-335.

Kar et al., (2014) Synthesis and characterization of Cu/Ag nanoparticle loaded mullite nanocomposite system: A potential candidate for antimicrobial and therapeutic applications. Biochim Biophys Acta 1840(11): 3264-3276.

Malnick et al., (2008) Pyjamas and sheets as a potential source of nosocomial pathogens. Journal of Hospital Infection 70(1): 89-92.

Mumcuoglu et al., (2008) Copper oxide-impregnated fabrics for the control of house dust mites. International Journal of Pest Management 54(3): 235-240.

English abstract and machine translation for JP S54-151669, printed 2018.

Silver(ii) oxide; Material Safety Data Sheet. Retrieved from: https://fscimage.fishersci.com/msds/31967.htm on Mar. 11, 2019 (Mar. 11, 2019). 5 pages.

Silver Oxide. Material Safety Data Sheet. Retrieved from: https://fscimage.fishersci.com/msds/20819.htm on Mar. 11, 2019 (Mar. 11, 2019), 5 pages.

ANTIMICROBIAL MATERIAL COMPRISING SYNERGISTIC COMBINATIONS OF METAL OXIDES

CROSS-REFERENCE TO RELATED APPLICATIONS

This application is a Continuation of U.S. application Ser. No. 15/549,018, filed Aug. 4, 2017, which is a National Phase Application of PCT/IL2015/050142, filed Feb. 8, 2015; the contents of all of which are incorporated herein by reference in their entirety.

FIELD OF THE INVENTION

The present invention relates to materials comprising a polymer having a synergistic combination of metal oxides incorporated within the polymer, the materials having antimicrobial properties.

BACKGROUND OF THE INVENTION

It is widely known that crowded places (such as hospitals, healthcare facilities, food processing plants, hotels, dormitories, and public transportation) bear the potential risk of transferring diseases. Hence such places require use of products which are less prone to microbe and pathogen proliferation. As microbes evolve to be more pathogenic and drug resistant, the need to keep the bio-burden levels under control has increased, and more effective avenues of control need to be developed.

On many hospital items and equipment the presence of microorganisms in the hospital environment can lead to healthcare associated infections (HAIs). Even with all present-day cleaning and disinfection solutions, in the United States 4.5% of hospitalized patients develop HAI, resulting in an estimated 100,000 deaths annually and adding 35.7 to 45 billion dollars to healthcare costs. Bacteria and other microorganisms can evade routine cleaning which cannot provide long term protection against microorganisms. What is needed is a fast-acting, continuous (not episodic) supplement to conventional cleaning. It should also be inexpensive without compromising on efficacy, as healthcare institutions have very tight budgets.

It has previously been shown that certain individual metal oxides, when exposed to moisture, will release ions to the environment in which the metal oxide is exposed. It is also known that these ions have antimicrobial, antiviral, and anti-fungal properties (Borkow and Gabbay, FASEB J. 2004 November; 18(14):1728-30), as well as anti-mite qualities (Mumchuoglu, Gabbay, Borkow, International Journal of Pest Management, Vol. 54, No. 3, July-September 2008, 235-240).

U.S. Pat. No. 6,124,221 discloses an article of clothing having antibacterial, antifungal, and anti-yeast properties, comprising at least a panel of a metalized textile, said textile including fibers selected from the group consisting of natural fibers, synthetic cellulosic fibers, regenerated protein fibers, acrylic fibers, polyolefin fibers, polyurethane fibers, vinyl fibers, and blends thereof, and having a plating including an antibacterial, antifungal and anti-yeast effective amount of at least one oxidant cationic species of copper wherein the plating is bonded directly to the fibers.

U.S. Pat. No. 6,482,424 discloses a method for combating and preventing nosocomial infections, comprising providing to health care facilities textile fabrics incorporating fibers coated with an oxidant, cationic form of copper, for use in patient contact and care, wherein the textile fabric is effective for the inactivation of antibiotic resistant strains of bacteria.

U.S. Pat. No. 7,169,402 encompasses antimicrobial and antiviral polymeric materials, comprising a polymer selected from the group consisting of polyamide, polyester, and polypropylene, and a single antimicrobial and antiviral component consisting essentially of microscopic water insoluble particles of copper oxide incorporated in the polymer, wherein a portion of said particles in said polymer are exposed and protruding from the surface of the material, and wherein said particles release $Cu^{2+}$ when exposed to water or water vapor.

US Patent Application Publication No. 2008/0193496 discloses polymeric master batch for preparing an antimicrobial and antifungal and antiviral polymeric material comprising a slurry of thermoplastic resin, an antimicrobial and antifungal and antiviral agent consisting essentially of water insoluble particles of ionic copper oxide, a polymeric wax and an agent for occupying the charge of said ionic copper oxide.

U.S. Pat. No. 7,364,756 discloses a method for imparting antiviral properties to a hydrophilic polymeric material comprising preparing a hydrophilic polymeric slurry, dispersing an ionic copper powder mixture containing cuprous oxide and cupric oxide in said slurry and then extruding or molding said slurry to form a hydrophilic polymeric material, wherein water-insoluble particles that release both $Cu^{++}$ and $Cu^{+}$ are directly and completely encapsulated within said hydrophilic polymeric material.

Similar findings on antimicrobial activity of metal oxides have also been published in connection to tetrasilver tetroxide as a mixed oxidation state compound as cited in various publications and patents by Antelman.

U.S. Pat. No. 6,645,531 to Antelman discloses pharmaceutical compositions that include a therapeutically effective amount of at least one electron active compound, or a pharmaceutically acceptable derivative thereof, that has at least two polyvalent cations, at least one of which has a first valence state and at least one of which has a second, different valence state. Preferred compounds include Bi(III,V) oxide, Co(II,III) oxide, Cu(I,III) oxide, Fe(II,III) oxide, Mn(II,III) oxide, and Pr(III,IV) oxide, and optionally Ag(I,III) oxide. Further provided are methods of halting, diminishing, or inhibiting the growth of at least one of a bacterium, a fungus; a parasitic microbe, and a virus, comprising administering to a human subject a therapeutically effective amount of the at least one electron active compound.

U.S. Pat. No. 6,436,420 to Antelman is related to fibrous textile articles possessing enhanced antimicrobial properties prepared by the deposition or interstitial precipitation of tetrasilver tetroxide ($Ag_4O_4$) crystals within the interstices of fibers, yarns and/or fabrics forming such articles.

There is an unmet need for a cost-effective material having improved antimicrobial and antiviral properties, which can be beneficially used in combating or inhibiting microbe activity and preventing or treating infections.

SUMMARY OF THE INVENTION

The present invention relates to materials having antimicrobial properties and methods for the preparation thereof. The antimicrobial material comprises a polymer and a synergistic combination of at least two metal oxide powders incorporated within the polymer, comprising a mixed oxidation state oxide and a single oxidation state oxide. The metal oxide powders are incorporated within the polymer such that upon hydration of the material, the ions of the two metal oxides are in ionic contact with each other.

The present invention is based in part on an unexpected discovery that the antimicrobial activity of a single oxidation state metal oxide is enhanced by the addition of a mixed oxidation state metal oxide, wherein the two metal ions are in ionic contact, such that the combination of the metal oxide particles provides a synergistic effect as compared to the activity of each of the metal oxides alone. It has further been surprisingly found that even the addition of the mixed oxidation state oxide in an amount of less than 10% wt. of the total weight of the combination provides synergistic antimicrobial effect.

Homogeneous incorporation of inorganic particles into a substrate, particularly a polymeric substrate, is challenged by particle agglomeration, chemical and physical interaction between the particles and the substrate and most of all by difference in the specific gravities of the particulate materials. However, materials of the present invention, which in some embodiments comprise particulate metal oxides having substantially different specific gravities, are generally characterized by a homogeneous distribution of the metal oxide powders within the polymer fiber. The present invention overcomes the problem imposed by use of distinct types of metal oxides by equalizing bulk densities of the metal oxide particles. Thus, according to some embodiments, the materials of the present invention comprise metal oxide powders, which, even though having substantially different specific gravities, have substantially similar bulk densities. Mean particle sizes of the metal oxides can be proportionally reduced in order to compensate for the difference in the specific gravities thereof and obtain substantially similar bulk densities. Alternatively, bulk densities of the metal oxides can be equalized by coating the metal oxide powders with a coating, which thickness or weigh is proportional to the specific gravity of the powders.

Therefore, according to one aspect, the present invention provides a material having antimicrobial properties, said material comprising a polymer having incorporated therein synergistic combination of at least two metal oxides comprising a mixed oxidation state oxide of a first metal and a single oxidation state oxide of a second metal, the powders being incorporated substantially uniformly within said polymer, wherein the powders have substantially different specific gravities and substantially similar bulk densities, and wherein the ions of the metal oxides are in ionic contact upon exposure of said material to moisture. According to some embodiments, the first metal and the second metal are different.

In some embodiments, the mixed oxidation state oxide is selected from the group consisting of tetrasilver tetroxide ($Ag_4O_4$), $Ag_3O_4$, $Ag_2O_2$, tetracopper tetroxide ($Cu_4O_4$), Cu (I,III) oxide, Cu (II,III) oxide, $Cu_4O_3$ and combinations thereof. Each possibility represents a separate embodiment of the invention. In further embodiments, the mixed oxidation state oxide is selected from the group consisting of tetrasilver tetroxide ($Ag_4O_4$), $Ag_2O_2$, tetracopper tetroxide ($Cu_4O_4$), Cu (I,III) oxide, Cu (II,III) oxide and combinations thereof. Each possibility represents a separate embodiment of the invention. In some embodiments, the single oxidation state oxide is selected from the group consisting of copper oxide, silver oxide, zinc oxide and combinations thereof.

Each possibility represents a separate embodiment of the invention. Copper oxide may be selected from the group consisting of cuprous oxide ($Cu_2O$), cupric oxide (CuO) and combinations thereof. Each possibility represents a separate embodiment of the invention. In particular embodiments, the combination of the at least two metal oxides comprises copper oxide and tetrasilver tetroxide. In further particular embodiments, copper oxide is cuprous oxide.

According to some embodiments, the mixed oxidation state oxide constitutes up to about 60% wt. of the total weight of the synergistic combination of the at least two metal oxide powders. According to further embodiments, the mixed oxidation state oxide constitutes up to about 15% wt. of the total weight of the synergistic combination of the at least two metal oxide powders.

According to still further embodiments, the mixed oxidation state oxide constitutes from about 0.5% to about 15% wt. of the total weight of the synergistic combination of the at least two metal oxide powders. According to yet further embodiments, the mixed oxidation state oxide constitutes about 1% wt. of the total weight of the synergistic combination of the at least two metal oxide powders.

According to some embodiments, the mixed oxidation state oxide constitutes from about 0.05% to about 15% wt. of the total weight of the synergistic combination of the at least two metal oxide powders. According to further embodiments, the mixed oxidation state oxide is present in the synergistic combination of the at least two metal oxide powders in a detectable amount. According to still further embodiments, the presence of the mixed oxidation state oxide in the material is detectable by means of an X-ray diffraction spectroscopy (XRD), electron microscopy, electron spectroscopy, Raman spectroscopy or electoanalytical methods. Each possibility represents a separate embodiment of the invention.

According to some embodiments, the metal oxides are not exposed on the surface of the material. According to other embodiments, the powders are distributed on the surface of the material in a generally uniform fashion. According to further embodiments, the metal oxide particles protrude from a surface of the material. In yet further embodiments, the metal oxide particles are attached to, deposited on or inserted into the surface of the material.

According to some embodiments, each of the metal oxide powders independently comprises particles, having a mean particle size of from about 1 nanometer to about 10 microns. According to other embodiments, each of the metal oxide powders independently comprises particles, which size is from about 10 nanometers to about 10 microns. According to further embodiments, each of the metal oxide powders independently comprises particles, which size is from about 0.5 to about 1.5 microns.

According to some embodiments, the metal oxide powders having the substantially similar bulk densities comprise particles which mean particle size is inversely proportional to the specific gravity thereof. According to other embodiments, the metal oxide powders having the substantially similar bulk densities comprise particles which have substantially similar mean particles sizes and wherein said particles are coated with a coating. According to further embodiments, the coating thickness is proportional to the specific gravity of the metal oxide particles. In alternative embodiments, the coating weight is proportional to the specific gravity of the metal oxide powders. According to further embodiments, the coating comprises polyester or polyalkene wax. The polyester or polyalkene wax may be selected from the group consisting of a polypropylene wax, oxidized polyethylene wax, ethylene homopolymer wax and a combination thereof. Each possibility represents a separate embodiment of the invention.

According to further embodiments, the metal oxide powders comprise particles, which are encapsulated within an encapsulating compound. The encapsulating compound may comprise silicate, acrylate, cellulose, derivatives thereof or combinations thereof. The non-limiting example of acrylate is poly(methyl methacrylate) (PMMA). According to the some exemplary embodiments, the encapsulating agent is a silicate or a poly(methyl methacrylate) (PMMA).

According to some embodiments, the material of the present invention further comprises a chelating agent or a metal deactivating agent associated with the metal oxide powders. The metal deactivating agent may be selected from the group consisting of phenolic antioxidant, potassium iodide, potassium bromide, calcium stearate, zinc stearate, aluminum stearate, tertiary chain extender and a combination thereof. Each possibility represents a separate embodiment of the invention.

According to further embodiments, the material of the present invention further comprises a surfactant associated with the metal oxide powder. The surfactant may include a sulfate, a sulfonate, a silicone, a silane, or a non-ionic surfactant. The non-limiting examples of commercially available surfactants include Sigma Aldrich Niaproof®, Dow Corning Xiameter® and Triton-X-100. The surfactant may further comprise a solvent, such as but not limited to, methyl alcohol, methyl ethyl ketone, or toluene. According to some embodiments, the material is devoid of the surfactant.

According to some embodiments, the material of the present invention comprises a polymer selected from a synthetic polymer, naturally occurring polymer or combinations thereof. Each possibility represents a separate embodiment of the invention. According to some embodiments, the synthetic polymer is selected from the group consisting of organic polymers, inorganic polymers and bioplastics. In further embodiments, the polymer is selected from the group consisting of polyamide, polyester, acrylic, polyalkene, polysiloxane, nitrile, polyvinyl acetate, starch-based polymer, cellulose-based polymer, dispersions and mixtures thereof. According to some currently preferred embodiments, the polymer is selected from polyester, polyalkene and polyamide. The polyalkene may be selected from the group consisting of polypropylene, polyethylene and combinations thereof. Each possibility represents a separate embodiment of the invention. According to particular embodiments, the polymer is selected from polyethylene, polypropylene, acrylonitrile butadiene styrene (ABS), polylactic acid (PLA), polyglycolic acid (PGA), poly(lactic-co-glycolic acid) (PLGA), poly(butyl acrylate) (PBA), polybutylene terephthalate (PBT) and combinations thereof. The polymer may be water based or solvent based.

According to some embodiments, the material of the present invention is selected from an intermediate-product, a semi-final product or a final product.

In some embodiments, the metal oxide powders are incorporated into the polymer by means of a master batch manufacturing process. Thus, according to some embodiments, the intermediate product is a master-batch.

According to some embodiments, the semi-final product comprises a fiber, a yarn, a textile, a fabric, a film or a foil. Each possibility represents a separate embodiment of the invention. The textile can be selected from a woven textile, a knit textile, a non-woven textile, a needle-punch textile or felt. Each possibility represents a separate embodiment of the invention. According to certain embodiments, the semi-final product is a fiber. The fiber can be a filament fiber or a staple fiber. According to some embodiments, the metal oxide powders are incorporated substantially uniformly within the fiber. The fiber can be formed into a yarn, textile or fabric.

According to some embodiments, the final product is a textile product or a non-textile polymeric article. According to some embodiments, the yarn, textile or fabric are formed into the textile product.

According to further embodiments, the polymer is formed into a semi-final product or a final product by means of extrusion, molding, casting or 3D printing. Each possibility represents a separate embodiment of the invention. According to some embodiments, the textile product comprises an extruded polymer. According to further embodiments, the semi-final product comprises an extruded polymer. According to certain embodiments, the fiber comprises an extruded polymer. According to additional embodiments, the non-textile polymeric article comprises an extruded, molded or cast polymer.

In some embodiments, the combined weight of the at least two metal oxides constitutes from about 0.25% to about 50% wt. of the total weight of the material.

In some embodiments, the material is in a form of a master batch. In further embodiments, the combined weight of the at least two metal oxides constitutes from about 0.5% to about 50% wt. of the total weight of the master batch. In yet further embodiments, the combined weight of the at least two metal oxides constitutes from about 20% to about 40% wt. of the total weight of the master batch.

In some embodiments, the material is in a form of a fiber, a yarn, a textile or a fabric. In certain such embodiments, the combined weight of the at least two metal oxides constitutes from about 0.5% to about 15% wt. of the total weight of the material.

According to some embodiments, the fiber is a polymeric fiber, being synthetic or semi-synthetic. According to some embodiments, the material further comprises a natural fiber. Thus, in some embodiments, the fiber is a blend of the polymeric fiber with a natural fiber.

According to further embodiments, the material comprises natural fiber is a weight percent of up to about 85% of the total weight of the material. In particular embodiments, the material comprises natural fiber is a weight percent of up to about 70% of the total weight of the textile product. The natural fiber may be selected from the group consisting of cotton, silk, wool, linen and combinations thereof. Each possibility represents a separate embodiment of the invention. In a certain embodiment, the material comprises cotton.

According to some embodiments, the material comprises the blend of a polymeric fiber and a natural fiber. In certain such embodiments, the combined weight of the at least two metal oxides constitutes from about 0.25% to about 5% wt. of the total weight of the material.

According to some embodiments, the material is in a form of a textile product or a non-textile polymeric article. Each possibility represents a separate embodiment of the invention. The textile product may be selected from clothing items, bedding textiles, laboratory or hospital textiles, medical textiles including bandages or sutures and textiles for internal use, or personal hygiene articles. The non-limiting examples of the textile products include pillowcases, eyemasks, gloves, socks, stockings, sleeves, shoe covers, slippers, undergarments, industrial uniforms, sportswear, towels, kitchen cloths, lab coats, floor cloths, sheets, bedding, curtains, textile covers, hard surface covers, diapers, incontinence pads, feminine hygiene products, gauze pads, monolithic extruded membranes, body-suits, trans-dermal patches, bandages, adhesive bandages, sutures, sheaths and textiles for internal use. The non-textile polymeric article may be selected from packaging or wrapping material, laboratory equipment, hospital equipment, preferably disposable hospital equipment, birth-control devices, agricultural products, covers for consumer items, and sanitary products. The non-limiting examples of the non-textile polymeric articles include food packages, gloves, blood bags, catheters, ventilation tubes, feeding tubes, transmission tubes, covers for mobile phones, pipes, toilet seats or toilet seat covers, kitchen sponges, working surface covers, and condoms. In certain embodiments, the material is in a form of a product selected from the group consisting of clothing items, bedding textiles, laboratory or hospital textiles, laboratory equipment, hospital equipment, medical textiles including bandages or sutures and textiles for internal use, personal hygiene articles, packaging or wrapping material, covers for consumer items, food equipment, birth-control devices, agricultural products, or sanitary products.

In some embodiments, the present invention provides the material for use in combating or inhibiting the activity of microbes or micro-organisms, selected from the group consisting of gram-positive bacteria, gram-negative bacteria, fungi, parasites, mold, spores, yeasts, protozoa, algae, acarii and viruses. Each possibility represents a separate embodiment of the invention.

According to some embodiments, the material is for use in combating healthcare associated infections, nosocomial infections or a combination thereof. Each possibility represents a separate embodiment of the invention.

Alternatively or additionally, the material of the present invention can be used for the treatment or prevention of atopic fungal, bacterial and viral infections. The infection may be selected from the group consisting of athlete's foot, yeast infections and staph infections. Each possibility represents a separate embodiment of the invention. In further embodiments, the material is for use in the treatment or prevention of topical viral infections. The infection may be selected from the group consisting of warts and Herpes B. Each possibility represents a separate embodiment of the invention.

In another aspect, the present invention provides a method for the preparation of a material having antimicrobial properties, said material comprising a polymer having incorporated therein a synergistic combination of at least two metal oxide powders, comprising a mixed oxidation state oxide of a first metal and a single oxidation state oxide of a second metal, the powders being incorporated substantially uniformly within said polymer, wherein the powders have substantially different specific gravities and substantially similar bulk densities, and wherein the ions of the metal oxides are in ionic contact upon exposure of said material to moisture, the method comprising the steps of:
  a. processing the at least two metal oxide powders to have substantially similar bulk densities; and
  b. mixing said powders with at least one polymer.

According to some embodiments, step a. comprises processing the metal oxide powders to obtain particles having mean particles sizes which are inversely proportional to the specific gravity thereof. In some embodiments, said processing comprises grinding.

According to other embodiments, step a. comprises processing the metal oxide powders to obtain particles having substantially similar sizes. In some embodiments, said processing comprises grinding. In additional embodiments, step a. further comprises applying a coating to the metal oxide powder particles. In some embodiments, step a. comprises applying a coating to the particles of at least one of the metal oxide powders. In further embodiments, step a. comprises applying a coating to the particles of each of the at least two metal oxide powders. In further embodiments, the coating thickness is proportional to the specific gravity of the metal oxide powders.

In some embodiments, the method further comprises a step of encapsulating the metal oxide powder particles within an encapsulating compound. In other embodiments, the method comprises a step of mixing the metal oxide powders with a metal deactivating agent or a chelating agent. In further embodiments, the method comprises a step of mixing the metal oxide powders with a surfactant.

According to further embodiments, step b. comprises producing a master batch, comprising the metal oxide powders and a carrier polymer. According to some embodiments, said at least one polymer comprises the carrier polymer. According to the preferred embodiments, the master batch is homogeneous. The master batch may be formed into pellets. Alternatively, the master batch may be formed into granules.

In some embodiments step b. further comprises adding the master batch to a polymer slurry. In further embodiments the polymer slurry comprises a polymer, which is the same as the carrier polymer. In other embodiments, the polymer slurry comprises a polymer, which is chemically compatible with the carrier polymer.

According to some embodiments, the method further comprises step c. comprising forming from the obtained mixture a film, a foil, a fiber, a yarn, a fiber, a textile, a textile product or a non-textile polymeric article. Each possibility represents a separate embodiment of the invention.

According to some particular embodiments, the method further comprises step c. comprising forming from the obtained mixture a film, a foil, a fiber, a yarn, a fiber or a textile, comprising said powders. Each possibility represents a separate embodiment of the invention. According to other particular embodiments, the method further comprises step c., comprising forming from the obtained mixture a textile product or a non-textile polymeric article, comprising said powders. Each possibility represents a separate embodiment of the invention.

In some embodiments, step c. comprises extrusion, molding, casting or 3D printing. In some exemplary embodiments step c. comprises extrusion. In further embodiments, extrusion comprises spinning through a spinneret. In the preferred embodiments, the material is homogeneously extruded. In other embodiments step c. comprises molding.

In some embodiments, step c. comprises forming a polymeric fiber from the mixture obtained in step b. In some embodiments, the method further comprises blending the polymer fiber with a natural fiber. In some embodiments, the method comprises forming the fiber into yarn, textile, fabric or a textile product.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIG. 5A—Bacteria proliferation inhibition between 0 and 40 minutes from the exposure of the fabric to the bacteria containing medium, FIG. 5B—Bacteria proliferation inhibition between 0 and 180 minutes from the exposure of the fabric to the bacteria containing medium, FIG. 5C—Bacteria proliferation inhibition between 0 and 300 minutes from the exposure of the fabric to the bacteria containing medium.

FIG. 6A—Bacteria proliferation inhibition between 0 and 40 minutes from the exposure of the fabric to the bacteria containing medium, and FIG. 6B—Bacteria proliferation inhibition between 0 and 180 minutes from the exposure of the fabric to the bacteria containing medium.

DETAILED DESCRIPTION

Figure 1A:
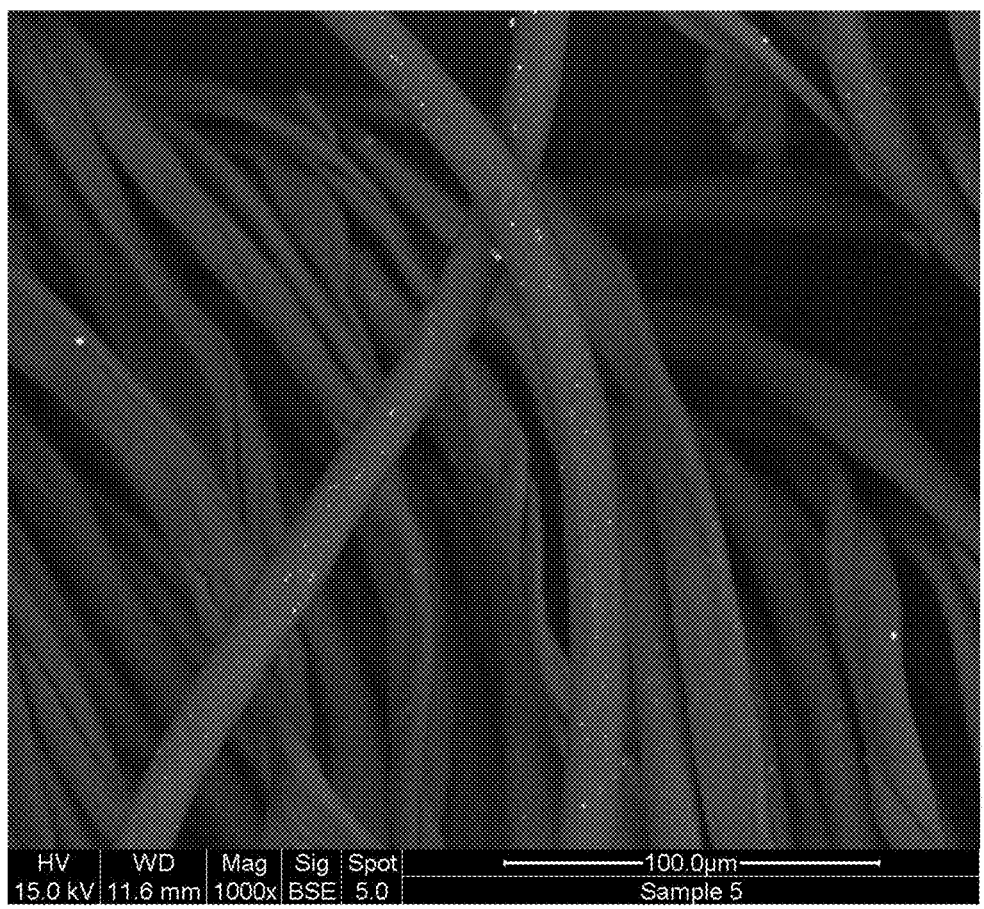
FIG. 1A: SEM micrograph of a polyester staple fiber containing copper oxide and tetrasilver tetroxide, prepared by a master batch preparation method, at 1000× magnification with protruding particles.

The present invention relates to materials having improved antimicrobial properties, including increased antibacterial, antiviral and antiparasitic activity, and to methods for preparation of said materials. The antimicrobial materials of the present invention comprise a polymer and a synergistic combination of at least two metal oxide powders homogeneously incorporated into said polymer.

As used herein, the term "antimicrobial" refers to an inhibiting, microcidal or oligodynamic effect against microbes, pathogens, and microorganisms, including but not limited to enveloped viruses, non-enveloped viruses, gram-positive bacteria, gram-negative bacteria, fungi, parasites, mold, yeasts, spores, algae, protozoa, acarii and dust mites, amongst others, and subsequent anti-odor properties.

According to some embodiments, the material of the present invention is selected from an intermediate-product, such as, but not limited to, a master batch; a semi-final product, for example, a fiber, a yarn, a textile, a fabric, a film or a foil; or a final product, including, inter alia, a textile product or a non-textile polymeric article.

The synergistic combination of the at least two metal oxide powders comprises a mixed oxidation state oxide of a first metal and a single oxidation state oxide of a second metal, wherein the powders have substantially similar bulk densities and wherein the ions of the metal oxides are in an ionic contact upon hydration of said material or its exposure to residual moisture.

As used herein, the term "ionic contact" refers to the ability of ions of each of the metal oxide powders, being incorporated within the polymer, to flow to a mutual aqueous reservoir upon exposure to said reservoir.

The Synergistic Combination of Two Metal Oxides

It has been surprisingly found that in order to improve antimicrobial properties of a single oxidation state metal oxide, a mixed oxidation state metal oxide compound should be added to the single oxidation state oxide. Without wishing to being bound by theory or mechanism of action, in order to provide the induced biocidal activity, the metal oxide particles should be mixed together in such a manner that the particles of each oxide are exposed to the same moisture reservoir, thus enabling a diffusion of ions from each metal oxide compound to the mutual moisture reservoir.

The synergistic combination of the two metal oxides, wherein at least one of the metal oxides is a mixed oxidation state oxide and at least one of the metal oxides is a single oxidation state oxide is a non-naturally occurring biologically active combination. According to some embodiments, said non-naturally occurring combination of metal oxides applied to a polymer substrate demonstrates greater ionic activity than the naturally occurring compounds alone. Without wishing to being bound by theory or mechanism of action, the increased ionic activity is responsible for a greater microcidal effect when compared to the equal amounts of naturally occurring metal oxide compounds under similar conditions.

As defined herein, the term "synergistic combination" refers to a combination of at least two metal oxides, which provides higher antimicrobial efficiency than the equal amount of each of the metal oxides alone. The higher antimicrobial efficiency may relate to accelerated bacteria or micro-organism killing rate.

The synergistic combination applied to a polymer comprises two or more biologically active relatively insoluble metal oxides, wherein at least one metal oxide is selected from single oxidation state oxide compounds, and at least one metal oxide is selected from mixed oxidation state oxide compounds has been found to be biologically active by itself and synergistic, providing surprisingly accelerated microbe mortality as compared to the same single and mixed oxidation state metal oxides individually, or combined within the single oxidation state group which are naturally occurring.

As used herein, the term "mixed oxidation state" refers to atoms, ions or molecules in which the electrons are to some extent delocalized via various electronic transition mechanisms and are shared amongst the atoms, creating a conjugated bond which affects the physiochemical properties of the material. In the mixed oxidation state, electronic transitions form a superposition between two single oxidation states. This can be expressed as any metal that has more than a single oxidation state coexisting, as in the formula X (Y, Z), where X is the metal element and Y and Z are the oxidation states, where Y≠Z. The mixed oxidation state oxide may be one compound, wherein metal ions are in different oxidation states (i.e. X(Y,Z)).

According to some embodiments, the mixed oxidation state oxide useful in the materials of the present invention is selected from the group consisting of tetrasilver tetroxide (TST)—$Ag_4O_4$ (Ag I, III), $Ag_3O_4$, $Ag_2O_2$, tetracopper tetroxide—$Cu_4O_4$ (Cu I, III), $Cu_4O_3$, Cu (I, II), Cu (II, III), Co(II,III), Pr(III,IV), Bi(III,V), Fe(II,III), and Mn(II,III) oxides and combinations thereof. Each possibility represents a separate embodiment of the invention. In certain embodiments, the material comprises a mixed oxidation state oxide selected from the group consisting of tetrasilver tetroxide, tetracopper tetroxide and a combination thereof.

As used herein, the term "single oxidation state" refers to atoms, ions or molecules in which same types of atoms are present in one oxidation state only. For example, in copper (I) oxide copper all ions are in the oxidation state +1, in copper (II) oxide all copper ions are in the oxidation state +2 and in zinc oxide all zinc ions are in oxidation state +2.

According to some embodiments, the single oxidation state oxide useful in the materials of the present invention is selected from the group consisting of copper oxide, silver oxide, zinc oxide and combinations thereof.

As used herein, the term "copper oxide" refers to either or both of copper oxide's multiple oxidation states: the first, principal single oxidation state cuprous oxide (($Cu_2O$), also identified as copper (I) oxide); or the second, higher single oxidation state cupric oxide ((CuO), also identified as copper (II) oxide) either individually or in varying proportions of the two naturally occurring oxidation states.

As used herein, the term "silver oxide" refers to silver oxide's multiple oxidation states: the first, principal single oxidation state $Ag_2O$ (also identified as silver (I) oxide); or the second, higher single oxidation state AgO, (also identified as silver (II) oxide); or the third highest single oxidation state $Ag_2O_3$, individually or in any varying proportion of these three naturally occurring oxidation states.

As used herein, the term "zinc oxide" refers to zinc oxide's principal oxidation state $ZnO_2$.

According to some embodiments, copper oxide is selected from the group consisting of $Cu_2O$, CuO and combinations thereof. According to further embodiments, silver oxide is selected from the group consisting of $Ag_2O$, AgO, $Ag_2O_3$ and combinations thereof. Each possibility represents a separate embodiment of the invention.

In certain embodiments, the material comprises a single oxidation state oxide selected from the group consisting of copper oxide, silver oxide and a combination thereof. In further embodiments, the single oxidation state oxide is copper oxide. In still further embodiments, the material comprises a single oxidation state oxide selected from the group consisting of $Cu_2O$, CuO and combinations thereof. Each possibility represents a separate embodiment of the invention. In certain embodiments, copper oxide is $Cu_2O$.

According to some embodiments, the metal oxides useful in the materials of the present invention are selected from the group consisting of copper oxide, tetracopper tetroxide, silver oxide, tetrasilver tetroxide, zinc oxide and combinations thereof. According to further embodiments, the metal oxides are selected from the group consisting of $Cu_2O$, CuO, $Cu_4O_4$, $Ag_2O$, AgO, $Ag_2O_3$, $Ag_4O_4$, $ZnO_2$ and combinations thereof. In particular embodiments, the material comprises at least two metal oxides selected from the group consisting of copper oxide, tetrasilver tetroxide, tetracopper tetroxide and combinations thereof. In the currently preferred embodiments, the single oxidation state oxide is copper oxide and the mixed oxidation state oxide is tetrasilver tetroxide. In further embodiments, the single oxidation state oxide is cuprous oxide and the mixed oxidation state oxide is tetrasilver tetroxide.

Combinations of copper oxide and zinc oxide are not known to provide synergistic antimicrobial effect. While acceleration of the antimicrobial effects of a naturally occurring copper oxide comprising a mixture of cupric and cuprous oxides was disclosed, for example, in U.S. Pat. No. 7,169,402, the present invention provides for the first time non-naturally occurring combinations of metal oxides, specifically combinations comprising a single oxidation state oxide combined with tetracopper tetroxide or tetrasilver tetroxide, such combinations being characterized by synergistic antimicrobial proliferation properties. The synergistic effect of the compositions comprising a mixture of two different metal oxides, wherein at least one of the metal oxides is a mixed oxidation state oxide is even more surprising considering the biocidal activity of a combination of copper oxide and proven effective silver compound AlphaSan®, which was tested by the inventor of the present invention and presented in the experimental section. Addition of the silver compound AlphaSan® to $Cu_2O$ did not increase the biocidal rate thereof and no synergistic acceleration was observed. Only when a mixed oxidation state form of either silver ($Ag_4O_4$) was combined with a single oxidation state metal oxide comprising copper oxide, the antimicrobial properties of the single oxidation state metal oxide were enhanced. Said antimicrobial activity of the combination of the metal oxides was increased also as compared to the activity of the mixed oxidation state metal alone. Without wishing to being bound by theory or mechanism of action, the measured synergistic effect of such combinations can be attributed to intervalence charge transfer between the metal ions having different oxidation states. Exposure of the combination of the at least two metal oxides, comprising a mixed oxidation state oxide and a single oxidation state oxide, to a mutual moisture reservoir establishes ionic contact between the metal oxides and allows ion release from each metal oxide to the mutual moisture reservoir, thus providing acceleration of microbial mortality rates.

According to further embodiments, the material of the present invention comprises a synergistic combination of at least two metal oxides according to the principles of the present invention, wherein each of the metal oxides can be present in the combination at a weight percent of from about 0.05% to about 99.95%, such as from about 0.1% to about 99.9%, or from about 0.5% to about 99.5%. Each possibility represents a separate embodiment of the invention.

It has been surprisingly found that incorporation of a combination of a mixed oxidation state oxide and a single oxidation state oxide into a polymer, wherein the mixed oxidation state oxide is present in a weight percent of less than 10% in the total weight of the combination of the metal oxides was sufficient to cause the acceleration of antimicrobial activity of said polymer, as compared to each of the polymers comprising mixed oxidation state oxide and single oxidation state oxide alone. This was even more surprising since the total weight of the mixed oxidation state oxide in the polymer comprising the combination of the metal oxide powders was ten times lower than in the polymer comprising the mixed oxidation state alone.

Thus, according to some embodiments, the mixed oxidation state oxide constitutes from about 1% to about 20% wt. of the total weight of the combination of the two metal oxides. According to yet further embodiments, the mixed oxidation state oxide constitutes from about 5% to about 15% wt. of the total weight of the combination of the two metal oxides. According to still further embodiments, the mixed oxidation state oxide constitutes about 10% wt. of the total weight of the combination of the two metal oxides.

According to other embodiments, the mixed oxidation state oxide constitutes up to about 60% wt. of the total weight of the combination of the two metal oxides, such as up to about 50% wt., up to about 40% wt., up to about 30% wt., up to about 20% wt. or up to about 15% wt. of the total weight of the combination of the two metal oxides. Each possibility represents a separate embodiment of the invention.

It has been further discovered that a polymer comprising as low as 3% wt. of the mixed oxidation state oxide in the metal oxides combination had increased biocidal activity as compared to the polymer comprising the single oxidation state oxide alone at the same weight percent of the metal oxide in the polymer as the weight percent of the metal oxides combination. It was also surprisingly found that antimicrobial activity of the material comprising a combination of the two metal oxides was enhanced as compared to the biocidal activity of single oxidation state oxide, even when the combination comprised as low 0.5% wt. of the mixed oxidation state oxide. Therefore, the mixed oxidation state oxide can beneficially be used in the material in a relatively low concentration, as compared to the single oxidation state oxide, thereby increasing commercial viability of the material.

According to some embodiments, the mixed oxidation state oxide constitutes from about 0.05% to about 99.5% wt. of the total weight of the combination of the two metal oxides, such as from about 0.05% to about 90% wt., from about 0.05% to about 80% wt., from about 0.05% to about 70% wt., from about 0.05% to about 60% wt., from about 0.05% to about 50% wt., from about 0.05% to about 40% wt., from about 0.05% to about 30% wt., from about 0.05% to about 20% wt., or from about 0.05% to about 15% wt. of the total weight of the combination of the two metal oxides. Each possibility represents a separate embodiment of the invention.

According to further embodiments, the mixed oxidation state oxide constitutes from about 0.05% to about 15% wt. of the total weight of the combination of the two metal oxides, such as from about 0.1% to about 15% wt., from about 0.5% to about 15% wt., from about 1% to about 5% wt., from about 0.5% to about 5% wt., or from about 0.1% to about 3% wt. of the total weight of the combination of the two metal oxides. Each possibility represents a separate embodiment of the invention.

According to particular embodiments, the mixed oxidation state oxide constitutes about 1% wt. of the total weight of the combination of the two metal oxides. According to further particular embodiments, the mixed oxidation state oxide constitutes about 0.5% wt. of the total weight of the combination of the two metal oxides. According to still further particular embodiments, the mixed oxidation state oxide constitutes about 0.1% wt. of the total weight of the combination of the two metal oxides. According to yet further particular embodiments, the mixed oxidation state oxide constitutes about 0.05% wt. of the total weight of the combination of the two metal oxides. According to some embodiments, the antimicrobial effect of the combination of the two metal oxides is synergistic.

According to some embodiments, the mixed oxidation state oxide is present in the synergistic combination of the metal oxide powders in a detectable amount. The presence of the mixed oxidation state oxide in the synergistic mixture can be detected by means of an X-ray diffraction spectroscopy (XRD), electron microscopy, electron spectroscopy, Raman spectroscopy or electoanalytical methods. Electron spectroscopy includes, inter alia, X-ray photoelectron spectroscopy (XPS), electron spectroscopy for chemical analysis (ESCA and Auger electron spectroscopy (AES). The non-limiting example of electron microscopy method suitable for the detection of mixed oxidation state oxide is Scanning electron microscopy (SEM), optionally conjugated with Energy-dispersive X-ray spectroscopy (EDS). According to certain embodiments, the presence of the mixed oxidation state oxide is detected by XRD.

The Metal Oxide Powders

The copper oxide useful in the materials of the present invention can be any commercially available copper oxide powder with a purity level of no less than 97% wt. In some exemplary embodiments, the powder is purchased from SCM Inc. of North Carolina, USA. Due to the prevalence of suppliers of this powder it is not economically viable to manufacture the powder. The zinc oxide useful in the materials of the present invention can be any commercially available zinc oxide powder with a recommended purity level of no less than 98% wt. which is readily available commercially. However, due to the difficulty in obtaining tetrasilver tetroxide and/or tetracopper tetroxide, it is necessary to synthesize the specific species as described hereinbelow.

According to some embodiments, the particle size of the commercially available metal oxide powder is from about 10 to about 20 micron. The metal oxide powder can be ground to a particle size of from about 1 nanometer to about 10 micron. Accordingly, the size of the metal oxide particles in the materials of the present invention can be from about 1 nanometer to about 10 microns. According to some embodiments, the particle size is from about 1 to 10 micron. According to further embodiments, the particle size is from about 5 to about 8 micron. According to other further embodiments, the particle size is from about 0.1 to about 0.5 micron. According to further embodiments, the particle size is from about 0.25 to about 0.35 micron According to some embodiments, the metal oxide powders comprise agglomerates which are no larger than 20 microns. According to other embodiments, the metal oxide powders comprise agglomerates which are no larger than 10 microns. In other embodiments, the materials of the present invention are devoid of metal oxide particles agglomerates.

The Polymer

As used herein, the term "polymer" or "polymeric" refers to materials consisting of repeated building blocks called monomers. The polymer may be homogenous or heterogeneous in its form; hydrophilic or hydrophobic; natural, synthetic, mixed synthetic or bioplastic. The non-limiting examples of polymers suitable for incorporation of the metal oxide powders include, inter alia, polyamide, polyester, acrylic, isotactic compounds including but not limited to polypropylene, polyethylene, polyolefin, acrylic compounds, polyalkene, silicones, and nitrile; cellulose-based polymer or a mixture of different cellulose materials; converted cellulose mixed with plasticizers such as but not limited to rayon viscose, starch-based polymer, and acetate; petroleum derivatives and petroleum gels; fats, both synthetic and natural; polyurethane; natural latex; and mixtures and combinations thereof. Each possibility represents a separate embodiment of the invention.

According to some embodiments, the polymer is a synthetic polymer, including organic polymers, inorganic polymers and bioplastics. According to some embodiments, the polymer is selected from the group consisting of polyamide, polyester, acrylic, polyolefin, polysiloxane, nitrile, polyvinyl acetate, cellulose-based polymers, starch-based polymer, derivatives, dispersions and combinations thereof. Each possibility represents a separate embodiment of the invention. The non-limiting examples of the cellulose-based polymer are viscose or rayon. According to certain embodiments, the polymer is selected from the group consisting of polyamide, polyester, acrylic, polyalkene and combinations thereof. According to other embodiments, the polymer is selected from the group consisting of polyamide, polyalkene, polyurethane, polyester and combinations thereof. Each possibility represents a separate embodiment of the invention. According to particular embodiments, the polymer is selected from polyethylene, polypropylene, acrylonitrile butadiene styrene (ABS), polylactic acid (PLA), polyglycolic acid (PGA), poly(lactic-co-glycolic acid) (PLGA), poly(butyl acrylate) (PBA), polybutylene terephthalate (PBT) and combinations thereof. The polymer may be water based or solvent based.

Combinations of more than one of said materials can also be used provided they are compatible or adjusted for compatibility.

The Polymer Having the Metal Oxide Powders Incorporated Therein

According to some embodiments, the metal oxide powders are incorporated into the polymer by a master batch manufacturing.

As used herein, the term "master batch" unless otherwise indicated, refers to a carrier polymer containing metal oxide particles, formed into pellets or granules, wherein the polymer is compatible with the end product material. The master batch can be added as a chemical additive to a polymeric slurry comprising same or chemically compatible polymer before extrusion, molding, casting or 3D printing. Alternatively, the master batch can comprise a compounded resin containing the final dosage of the polymers and the metal oxides required for the product to be formed from the polymer.

Metal oxide powders can be included in a polymer using a master batch system so that the powder particles form part of the entire polymeric product. However, the currently known processes for the preparation of a polymeric material having antimicrobial properties are adapted for inclusion of a single type of metal oxide. The present invention provides materials comprising a combination of a mixed oxidation state oxide of a first metal and a single oxidation state oxide of a second metal. According to some exemplary embodiments, the first metal and the second metal are different. Thus, according to further embodiments, the at least two metal oxide powders have substantially different specific gravities.

When two or more particulate compounds having different specific gravities and being disruptive to non-isotactic materials, such as the majority of polymers, have to be incorporated into the polymeric material, control over suspension and dispersion of the particles in the polymeric slurry is complicated. Such slurries generally yield inhomogeneous extruded or cast polymers. Dispersion and suspension of distinct metal oxide powders is not usually practiced in master batch production, where normally a specific single compound is desired to be added to the polymer. Therefore, when reducing the invention to practice, it was required to develop a method allowing incorporation of at least two metal oxide powders having substantially different specific gravities into a polymer fiber. Furthermore, since the amount of any metal oxide powder that can be incorporated into a polymer is limited by the disruption effect of the metal oxide on cross polymerization of non-isotactic polymers or weakening of the carrier polymer, it was necessary to develop a method to accommodate a high amount of multiple metal oxides in these polymers. The present invention thus provides a process for the preparation of the material having antimicrobial properties, providing control over the metal oxide particles concentration and distribution in the polymer. The present invention further provides materials having antimicrobial properties, comprising a combination of at least two metal oxide powders, wherein the metal oxide powders are incorporated within the polymer fiber in a generally uniform fashion. As used herein, the terms "generally uniform" or "homogeneous" that can be used interchangeably, denote that the volume percentage of the metal oxide particles on the polymer surface or in the bulk thereof varies by less than 20%, preferably less than 10%.

According to some embodiments, the materials of the present invention comprise at least two metal oxide powders having substantially different specific gravities. "Substantially different specific gravity" refers, in another embodiment, to the variance in the specific gravities of the at least two metal oxide powders, which is higher than about 5%. In another embodiment, the term refers to the variance of higher than about 10%. In yet another embodiment, the term refers to the variance of higher than about 15%.

To accommodate a plurality of metal oxide powders having distinct specific gravities in a single polymeric slurry, it is necessary to compensate for the particle weight differences of the metal oxides. In order to do so, the bulk densities of the metal oxide powders should be equalized. As used herein, the term "bulk density" refers to the mass of many particles of the powder divided by the total volume they occupy. According to some embodiments, the material comprises at least two metal oxides powders processed to have a substantially similar bulk density. "Substantially similar bulk density" refers, in some embodiments, to the variance in the bulk density of the at least two metal oxide powders, which is less than about 20%. In another embodiment, the term refers to the variance of less than about 10%. In yet another embodiment, the term refers to the variance of less than about 5%.

For example, specific gravity of copper oxide is 6.0 g/ml, wherein specific gravity of tetrasilver tetroxide is 7.48 g/ml. The bulk densities of the unprocessed copper oxide and the tetrasilver tetroxide powders are thus significantly different. Without wishing to being bound by theory or mechanism of action, in order to be incorporated into the polymer in a substantially uniform manner, the powders have to be processed to equalize the bulk densities thereof. Equalizing the bulk densities of the metal oxide powders can be achieved by altering the particle size of the metal oxide powders. Said particle size alteration can be performed by decreasing or increasing the particle size of the powders. For example, the particles size of the powders can be decreased by grinding and increased by applying a coating. The extent of the increase or decrease in the particle sizes of one metal oxide powder as compared to the other metal oxide powder is dependent on the specific gravities and/or the initial bulk densities of said metal oxide powders.

According to some embodiments, the metal oxide powders are processed by grinding. In other embodiments, the metal oxide powders are processed by milling. According to certain embodiments, the metal oxide powders are processed to have mean particle sizes which are inversely proportional to the specific gravities thereof. According to another embodiment, the metal oxide powders are ground to have mean particle sizes which are inversely proportional to the specific gravities thereof. According to the further embodiments, the mean particle sizes of the metal oxide powders are inversely proportional to the specific gravity thereof.

According to further embodiments, the material comprises at least two metal oxide powders having essentially similar particle sizes. "Substantially similar particle size" refers, in another embodiment, to the variance in the particle size of the at least two metal oxide powders which is less than about 20%. In another embodiment, the term refers to the variance of less than about 10%. In yet another embodiment, the term refers to the variance of less than about 5%. In still another embodiment, the term refers to the variance of less than about 1%.

According to further embodiments, the metal oxide powders are processed to have substantially similar particle sizes. According to further embodiments, the metal oxide powders are ground to have substantially similar particle sizes. According to yet further embodiments, at least one of the metal oxide powders is ground to obtain the at least two metal powders having substantially similar particle sizes.

According to some embodiments, the particles of at least one metal oxide powder comprise a coating. According to other embodiments, the particles of at least two metal oxide powders comprise the coating. In some embodiments, at least one of the metal oxide powders is processed to have coated particles. In further embodiments, each of the at least two metal oxide powders is processed to have coated particles. According to certain embodiments, said particles have substantially similar sizes. According to further embodiments, the coating thickness is proportional to the specific gravity of the metal oxide powders. According to yet further embodiments, the coating weight is proportional to the specific gravity of the metal oxide powders. According to some embodiments, the at least two metal oxide powders comprise particles having a different coating material. The molecular or specific weight of the coating material can be adjusted to compensate for the difference in the specific gravities of the metal oxide powders.

The metal oxide particles coating may comprise polyester or polyalkene wax. The non-limiting examples of the polyalkene wax include polypropylene wax marketed by Clariant as Licowax PP 230, an oxidized polyethylene wax marketed by Clariant as Licowax PED 521, an oxidized polyethylene wax marketed by Clariant as Licowax PED 121 or an ethylene homopolymer wax marketed by BASF as Luwax®.

According to further embodiments, the coating material comprises a copolymer of polyethylene wax and maleic anhydride. According to yet further embodiments, the coating material further comprises ionomers of low molecular weight waxes. According to additional embodiments, the polyethylene wax has a high wettability. In some embodiments, the coating material comprises homopolymers, oxidized homopolymers, high density oxidized homopolymers and co-polymers of polyethylene, polypropylene and ionomer waxes, micronized polyalkene waxes or mixtures thereof, as well as co-polymers of ethylene-acrylic acid and ethylene-vinyl acetate.

A critical prerequisite for the usability of such an additive concentrate is the correct choice of the wax component. Although it is not colored itself, it influences the performance of the additive concentrate. For more detailed information, reference may be made, for example, to the product brochure "Luwaxe®—Anwendung in Pigmentkonzentraten" about polyethylene waxes from BASF AG.

According to some embodiments, the weight of the coating material applied to the powder constitutes from about 0.2% to about 2% wt. of the metal oxide powder weight. According to additional embodiments, the weight of the coating material constitutes from about 0.2% to about 1% wt. of the metal oxide powder weight, preferably from about 0.4 to about 0.5% wt. Each possibility represents a separate embodiment of the invention. In a certain embodiment, the weight of the coating material constitutes about 1% wt. of the metal oxide powder weight.

According to other embodiments, the first metal and the second metal are the same. According to further embodiments, the at least two metal powders have substantially similar bulk densities.

Without wishing to being bound by theory or mechanism of action, in order to hinder a chemical interaction between the metal oxide powders and the carrier polymer or the polymer fiber, the metal oxides should be pretreated with an encapsulating compound. Said compounds isolate the metal oxides so that they will not interact with the polymeric material and are configured to abrade off the powder during product use. Thus, according to some embodiments, the materials of the present invention comprise metal oxide powders, comprising particles encapsulated within an encapsulating compound. The encapsulating compound can be selected from the group consisting of silicates, acrylates, cellulose, protein-based compounds, peptide-based compounds, derivatives and combinations thereof. In some embodiments, the encapsulating compound is selected from the group consisting of silicate, poly(methyl methacrylate) (PMMA) and a combination thereof.

According to some embodiments, the weight of the encapsulating compound applied to the powder constitutes from about 0.2% to about 2% wt. of the metal oxide powder weight. According to additional embodiments, the weight of the encapsulating compound constitutes from about 0.2% to about 1% wt. of the metal oxide powder weight, preferably from about 0.4 to about 0.5% wt. Each possibility represents a separate embodiment of the invention.

Additionally or alternatively, the chemical interaction between the metal oxide powders and the carrier polymer or the polymeric support, can be hindered through addition of metal deactivating agents or chelating agents. As used herein, the terms "metal deactivating agents" and "chelating agents" that can be used interchangeably, refer to an agent generally comprising organic molecules containing heteroatoms or functional groups such as a hydroxyl or carboxyl, the agent acting by chelation of the metal to form inactive or stable complexes.

Thus, according to some embodiments, the materials of the present invention comprise a metal deactivating agent or a chelating agent. In further embodiments, the materials of the present invention comprise a metal deactivating agent or a chelating agent associated with the metal oxide powders. The non-limiting example of the said metal deactivating agents and/or chelating agents include a phenolic antioxidant, potassium iodide, potassium bromide, calcium stearate, zinc stearate, aluminum stearate, tertiary chain extenders and combinations thereof. According to a particular embodiment, the metal deactivating agent is a phenolic antioxidant. The phenolic antioxidant can be selected from, but not limited to 2',3-bis [[3-[3,5-di-tert-butyl-4-hydroxyphenyl] propionyl]] propionohydrazide marketed under the name Irganox® MD 1024 by CIBA; Vitamin E (alpha-tocopherol) which is a high molecular weight phenolic antioxidant, marketed under the name Irganox® E 201 by CIBA; Irganox® B 1171, marketed by CIBA, which is a blend of a hindered phenolic antioxidant and a phosphate; and combination thereof. According to certain embodiments, the metal deactivating agents abrade off the metal oxide particles upon hydration of the material.

According to some embodiments, the weight of the metal deactivating agent applied to the powders constitutes from about 0.2% to about 5% wt. of the metal oxide powder weight. According to additional embodiments, the weight of the metal deactivating agent comprises from about 0.5% to about 1% wt. of the metal oxide powder weight. In a certain embodiment, the weight of the metal deactivating agent constitutes about 1% wt. of the metal oxide powder weight.

Another difficulty in adding almost any inorganic compound to a polymeric material is particle agglomeration. According to some embodiments, the metal oxide particles of the present invention are treated by a surfactant to prevent metal oxide particles agglomeration. Therefore, according to some embodiments, the materials of the present invention comprise a surfactant. In further embodiments, the materials comprise a surfactant associated with the metal oxide powders. The non-limiting examples of the surfactant include but are not limited to Sigma Aldrich Niaproof®, Dow Corning Xiameter® and Triton-X-100.

According to some embodiments, the weight of the surfactant constitutes from about 0.05% to about 2% wt. of the metal oxide powder weight. In a certain embodiment, the weight of the surfactant constitutes about 0.5% wt. of the metal oxide powder weight.

According to some embodiments, the metal oxide powders are present in the master batch at a weigh percent of from about 0.5% to about 95% of the total weigh of the master batch. According to further embodiments, the metal oxide powders are present in the master batch at a weigh percent of from about 5% to about 50%, preferably from about 20% to about 40%. Each possibility represents a separate embodiment of the invention. According to some embodiments, the master batch is prepared for direct extrusion, molding or casting, without further mixing with an additional polymer. In certain such embodiments, the metal oxide powders are present in the master batch at a weigh percent of from about 0.5% to about 30% of the total weigh of the master batch, preferably from about 0.5% to about 15% of the total weigh of the master batch. According to further embodiments, the metal oxide powders are present in the master batch in an amount configured to provide from about 0.5% wt. to about 30% wt. of the metal oxide particles in the material obtained through a master batch manufacture process, preferably from about 0.5% wt. to about 15% wt., or from about 1% wt. to about 5% wt. of the metal oxides of the total weight of the material. Each possibility represents a separate embodiment of the invention.

The composition of the master batch, comprising the polymer and the synergistic composition of the metal oxides can be formed into a semi-final or a final product. The semi-final product may include, inter alia, a fiber, a yarn, a textile, a fabric, a film or a foil; and the final product may include, inter alia a textile product or a non-textile polymeric article. According to some embodiments, the fiber is a polymeric fiber, being synthetic or semi-synthetic. The fiber may be a staple fiber or a filament fiber. According to some embodiments, the master batch composition is formed into a semi-final or final product by means of extrusion, molding, casting or 3D printing of the polymer, comprising said synergistic combination. According to further embodiments, the material is selected from an extruded, molded, cast or 3D printed polymer. Each possibility represents a separate embodiment of the invention.

Thus, in some embodiments, the metal oxide powders are present in the master batch in an amount configured to provide from about 0.5% to about 30% wt. of the metal oxide particles in the extruded or molded polymer obtained through a master batch manufacture process, preferably from about 0.5% wt. to about 15% wt., or from about 1% wt. to about 5% wt. of the metal oxides of the total weight of the extruded or molded polymer. Each possibility represents a separate embodiment of the invention. In still further embodiments, the metal oxide powders are present in the master batch in an amount configured to provide from about 0.5% to about 30% wt. of the metal oxide particles in the polymer fiber obtained through a master batch manufacture process, preferably from about 0.5% wt. to about 15% wt., or from about 1% wt. to about 5% wt. of the metal oxides of the total weight of the total weight of the polymer fiber. Each possibility represents a separate embodiment of the invention.

In some embodiments, the combined weight of the at least two metal oxides constitutes from about 0.25% to about 50% wt. of the total weigh of the materials.

In some embodiments, the material is in a form of a semi-final product, selected from a fiber, a yarn, a textile, a fabric, a film or a foil. In certain such embodiments, the combined weight of the at least two metal oxides constitutes from about 0.5% to about 30% wt. of the total weight of the semi-final product.

According to further embodiments, the combined weight of the at least two metal oxides constitutes from about 1% to about 15% wt. of the total weight of the semi-final product. In certain such embodiments, the polymer is selected from polyester or polyamide. In further embodiments, the semi-final product is a fiber, preferably including a staple fiber. According to certain embodiments, the combined weight of the at least two metal oxides constitutes from about 1% to about 5% wt. of the total weight of the semi-final product. According to other embodiments, the combined weight of the at least two metal oxides constitutes from about 3% to about 8% wt. of the total weight of the semi-final product.

According to further embodiments, the combined weight of the at least two metal oxides constitutes from about 0.5% to about 8% wt. of the total weight of the semi-final product. In certain such embodiments, the polymer is selected from polyester or polyamide. In further embodiments, the semi-final product is a fiber, preferably including a filament fiber. According to certain embodiments, the combined weight of the at least two metal oxides constitutes from about 1% to about 4% wt. of the total weight of the semi-final product. According to other embodiments, the combined weight of the at least two metal oxides constitutes from about 0.5% to about 2% wt. of the total weight of the semi-final product.

According to further embodiments, the combined weight of the at least two metal oxides constitutes from about 10% to about 30% wt. of the total weight of the semi-final product. In certain such embodiments, the polymer is a polyalkene. In further embodiments, the semi-final product is a fiber.

In some embodiments, the combined weight of the at least two metal oxide powders constitutes from about 3% to about 8% wt. of the total weight of material and the size of the metal oxide particles is from about 0.5 to about 1 micron. In particular embodiments, the combined weight of the at least two metal oxide powders constitutes about 3% wt. of the total weight of material, wherein the metal oxide particles size is about 1 micron. In other embodiments, the combined weight of the metal oxides powders constitutes about 8% wt. of the total weight of material, wherein the metal oxide particles size is about 0.5 micron.

In some embodiments, the polymer fiber is blended with a natural fiber. The natural fiber may be selected from the group consisting of cotton, silk, wool, linen and combinations thereof. In additional embodiments, the material further comprises a modified cellulose fiber. The non-limiting examples of cellulose modified fiber include viscose and rayon.

According to some embodiments, the natural fiber may be present in the material in a weight percent of up to about 95% of the total weight of the material. In further embodiments, the material of the present invention comprises from about 50% to about 85% wt. of natural fiber. According to some exemplary embodiment, the natural fiber may be present in the material in a weight percent of about 70% of the total weight of the material. According to further embodiments, the weight ratio between the polymer fiber with at least two metal powders incorporated therein and the natural fiber is from about 1:1 to about 1:6. The blend material therefore may comprise from about 50% wt. natural fiber/50% wt. polymer fiber to about 85% wt. natural fiber/15% wt. polymer fiber. In certain embodiments, the material comprises from about 50% wt. cotton/50% wt. polymer fiber to about 85% wt. cotton/15% wt. polymer fiber.

According to some embodiments, the material comprises a semi-final product comprising ta blend of a polymeric fiber and a natural fiber. In certain such embodiments, the combined weight of the at least two metal oxides constitutes from about 0.25% to about 5% wt. of the total weight of the semi-final product.

In some embodiments, the material comprises 100% wt. polymer fiber with at least two metal powders incorporated therein. Therefore, the material of the present invention can be devoid of natural fibers.

According to some embodiments, the weight of the mixed oxidation state oxide constitutes from about 0.001% to about 30% wt. of the total weight of the material. In some embodiments, the mixed oxidation state metal oxide constitutes from about 0.05% to about 2.5% wt. of the total weight of the material, preferably from about 0.1% to about 1% wt. of the total weight of the material. Each possibility represents a separate embodiment of the invention. The material can be selected from an intermediate, semi-final and final material.

According to some embodiments, the material having antimicrobial properties comprises the polymer and a synergistic combination of the at least two metal oxide powders, wherein the powders are incorporated within the polymer. According to some embodiments, the metal oxides powders are attached to the polymer. According to further embodiments, the powders are attached to the polymer surface. According to other embodiments, the powders are embedded into the polymer. According to further embodiments, the powders are embedded into the polymer surface. According to other embodiments, the powders are deposited on the polymer surface. According to additional embodiments, the powders are inserted into the polymer. According to further embodiments, the powders are inserted into the polymer surface. According to further embodiments, the metal oxide powders particles protrude from the polymer surface. According to still further embodiments, at least part of the metal oxide powders particles protrudes from the polymer surface. According to some embodiments, at least 10% of the synergistic combination of the metal oxides is present on the surface of the polymer. According to further embodiments, at least 5% of the synergistic combination of the metal oxides is present on the surface of the polymer. It has been found that as little as 1% appearance on the surface of a polymeric fiber, which contains particles protruding from the polymer surface, was sufficient to ensure a biocidal effect. Thus, according to some embodiments, at least 1% of the synergistic combination of the metal oxides is present on the surface of the polymer. According to other embodiments, the powders are not exposed on the surface of the polymer. According to some embodiments, said polymer is an extruded, cast or molded polymer or is in a form of a polymer fiber, a textile product or a non-textile polymeric article. Each possibility represents a separate embodiment of the invention.

The End Product

The materials of the present invention comprise a polymer and at least two metal powders incorporated therein, wherein the polymer can be an extruded, molded, cast or 3D printed polymer. According to some embodiments, said polymer is a molded polymer. In other embodiments, the polymer is an extruded polymer. In certain embodiments, the polymer is a form of a fiber. According to some embodiments, the fiber can be formed into a yarn, textile or fabric. According to some embodiments, the textile is selected from a woven textile, a knit textile, a non-woven textile, a needle-punch textile or felt.

According to certain embodiments, the final product includes a monolithic layer obtained by stacking of nano-denier fibers such as those produced using an electro-spinning process, said fibers comprising said synergistic combination of the metal oxide powders. In some embodiments, the metal oxide particles are disposed between the nano-fibers in the sheaths.

Also provided according to some embodiments of the present invention is an extruded polymer in the form of a staple or a filament fiber, comprising said metal oxide particles incorporated into a polymer fiber and formed as a non-extruded non-woven material or filling.

According to further embodiments, the semi-final product can be formed into a final product. According to some embodiments, final products of the present invention have a soft surface. The term "soft surface" as used herein, refers to all surfaces which are solid but are not hard surfaces, and most often refers to products made from knit, woven, or non-woven textile products. The final products of the present invention include, but are not limited to, textile products and non-textile polymeric articles.

The textile product may be selected from, but not limited to, clothing items, bedding textiles, laboratory or hospital textiles, medical textiles including bandages or sutures and textiles for internal use, and personal hygiene articles. The non-limiting examples of the textile products include pillowcases, eye-masks, gloves, socks, stockings, sleeves, shoe covers, slippers, undergarments, industrial uniforms, sportswear, towels, kitchen cloths, lab coats, floor cloths, sheets, bedding, curtains, textile covers, hard surface covers, diapers, incontinence pads, feminine hygiene products, gauze pads, monolithic extruded membranes, body-suits, transdermal patches, bandages, adhesive bandages, sutures, sheaths and textiles for internal use, compression garments in all sizes for different parts of the body, and absorbent pads.

The non-textile polymeric article may be selected from, but not limited to, packaging and wrapping material, laboratory equipment, hospital equipment, preferably disposable hospital equipment, covers for consumer items, food equipment, agricultural products, sanitary products or birth-control devices. The non-limiting examples of the non-textile polymeric articles include food packages, gloves, blood bags, catheters, ventilation tubes, feeding tubes, transmission tubes, covers for mobile phones, pipes, toilet seats or toilet seat covers, kitchen sponges, working surface covers, and condoms.

Products formed from the materials of the present invention, possess effective antimicrobial properties, including, but not limited to antimicrobial, antibacterial, antiviral, anti-fungal, and anti-mite properties.

Thus, according to some embodiments, the present invention provides the material for use in combating or inhibiting the activity of microbes or micro-organisms, selected from the group consisting of gram-positive bacteria, gram-negative bacteria, fungi, parasites, mold, spores, yeasts, protozoa, algae, acarii and viruses. Each possibility represents a separate embodiment of the invention. According to some embodiments, the present invention provides a method for combating or inhibiting the activity of microbes or micro-organisms, the method comprising providing to health care facilities the material according to the principles of the invention.

According to some embodiments, the material is for use in combating healthcare associated infections, nosocomial infections or a combination thereof. According to some embodiments, the present invention provides a method for combating healthcare associated infections, nosocomial infections or a combination thereof, the method comprising providing to health care facilities the material according to the principles of the invention.

The materials of the present invention can be particularly applicable in controlling hospital acquired infections, odor reduction in garments, socks, stockings and underclothing, in wound healing articles such as gauze, wound coverings, disposable sanitary products, disposable diapers, and sutures, single use garments, diapers and articles of clothing that can come in contact with a wound.

Alternatively or additionally, the material of the present invention can be used for the treatment or prevention of atopic fungal, bacterial and viral infections. The infection may be selected from the group consisting of athlete's foot, yeast infections and staph infections. In further embodiments, the material is used for the treatment or prevention of topical viral infections. The infection may be selected from the group consisting of warts and Herpes B. According to some embodiments, the present invention provides a method of treatment or prevention of atopic fungal, bacterial and viral infections, the method comprising topically applying to the body of the subject in need of such treatment the material according to the principles of the invention.

Thus, also provided according to the principles of the present invention is a product, preferably a textile product, used for the control of topical fungal infections, yeast infections and/or for topical viral control. In some embodiments, the metal oxide powders incorporated into the polymer may further be included in a film, fiber, textile patch and form that can be placed on the infected area, said form being selected from the group consisting of socks, panties, underwear, sleeves and patches. According to some embodiments, the metal oxide particles are incorporated into a fiber which is included in a substrate or textile made from a film, a non-woven material or a textile substrate for use in combating dust mites.

Preparation Method

In another aspect, the present invention provides a method for the preparation of the material according to the principles of the present invention, the method comprising the steps of:
  a. processing the at least two metal oxide powders to have substantially similar bulk densities; and
  b. mixing said powders with at least one polymer.

According to some embodiments, step a. comprises processing the metal oxide powders to obtain particles having sizes which are inversely proportional to the specific gravity thereof. According to some embodiments, step a. comprises reducing the metal oxide powders particle size to obtain particles having sizes which are inversely proportional to the specific gravity thereof. According to other embodiments, step a. comprises processing the metal oxide powders to obtain particles having substantially similar sizes. According to other embodiments, step a. comprises reducing the metal oxide powders particle size to obtain particles having substantially similar sizes. In some embodiments, said processing comprises grinding.

In additional embodiments, step a. further comprises applying a coating to the metal oxide powder particles. According to some embodiments, the coating thickness is proportional to the specific gravity of the metal oxide particles. According to other embodiments, the coating weight is proportional to the specific gravity of the metal oxide particles. According to some embodiments, the coating is applied to metal oxide powders having substantially similar particle sizes. According to further embodiments, the coating is applied to at least one metal oxide powder. According to other embodiments, the coating is applied to at least two metal oxide powders. According to further embodiments, the coating comprises polyester or polyalkene wax. The polyester or polyalkene wax may be selected from the group consisting of a polypropylene wax, oxidized polyethylene wax, ethylene homopolymer wax, and different types of waxes including copolymers of polyethylene wax and maleic anhydride which can also be used with ionomers of low molecular weight waxes or any combination thereof.

In some embodiments, the method further comprises a step of encapsulating the metal oxide powder particles within an encapsulating compound. In other embodiments, the method comprises a step of mixing the metal oxide powders with a metal deactivating agent or a chelating agent. In further embodiments, the method comprises a step of mixing the metal oxide powders with a surfactant. In some embodiments, the additional steps are performed prior to mixing the metal oxide powders with the polymer.

The encapsulating compound may be selected from the group consisting of silicate, acrylate, cellulose, derivatives thereof and combinations thereof. The metal deactivating agent may be selected from the group consisting of phenolic antioxidant, potassium iodide, potassium bromide, calcium stearate, zinc stearate, aluminum stearate, tertiary chain extender and a combination thereof.

In additional embodiments, the method comprises preparing the mixed oxidation state oxide. The mixed oxidation state oxide can be prepared by a standard procedure, for example as described by Hammer and Kleinberg in Inorganic Synthesis (IV,12) or in U.S. Pat. No. 5,336,416, which are incorporated by reference herein in their entirety. The method may further include a step of grinding the obtained mixed oxidation state oxide powder.

According to some embodiments, the mixing of the metal oxide powders and the at least one polymer is assisted by sonication. According to further embodiments, the metal oxide powders are mixed with a polymer fiber. According to still further embodiments, the metal oxide powders are embedded into the polymer fiber by means of sonication.

According to further embodiments, step b. comprises producing a master batch, comprising the metal oxide powders and a carrier polymer. According to some embodiments, said at least one polymer comprises the carrier polymer. According to the preferred embodiments, the master batch is homogeneous. According to additional embodiments, the metal oxide powders are distributed in the master batch in a generally uniform manner. The master batch may be formed into pellets. Alternatively, the master batch may be formed into granules. The carrier polymer may be selected from the group consisting of polyamide, polyalkene, polyurethane, polyester and combinations thereof.

In some embodiments step b. further comprises adding the master batch to a polymer slurry. In further embodiments the polymer slurry comprises a polymer, which is the same as the carrier polymer. In other embodiments, the polymer slurry comprises a polymer, which is chemically compatible with the carrier polymer. In some embodiments, the polymer is selected from the group consisting of polyamide, polyalkene, polyurethane and polyester. Combinations of more than one of said materials can also be used provided they are compatible or adjusted for compatibility. The polymeric raw materials are usually in bead form and can be mono-component, bi-component or multi-component in nature. The beads are heated to melting at a temperature which preferably will range from about 120° C. to 180° C. for isotactic polymers and up to 270° C. for polyester. The master batch is then added to the polymer slurry and allowed to spread through the heated slurry. The particle size of the metal oxide powders in these embodiments is preferably between 1 and 5 microns. However particulate size can be larger when the film or fiber thickness can accommodate larger particles.

According to some embodiments, the metal oxides are incorporated directly into the polymer fiber. According to further embodiments, particle size of the metal oxide powders is between 0.1 and 0.5 microns. According to still further embodiments, incorporation of the metal oxide powders into the polymer fiber is assisted by sonication.

According to some embodiments, the method further comprises step c. comprising forming from the obtained mixture a semi-final or a final product. Thus, in some embodiments, the method further comprises step c. comprising forming from the obtained mixture a film, a foil, a fiber, a yarn, a fiber or a textile, comprising said powders. Each possibility represents a separate embodiment of the invention. According to further embodiments, the method comprises a step of forming the film, foil, fiber, yarn, fiber or textile into a textile product or a non-textile polymeric article, In some embodiments, step c. comprises extrusion, molding, casting or 3D printing of the mixture obtained in step b. In some exemplary embodiments step c. comprises extrusion. In certain such embodiments, the polymer slurry is transferred to an extrusion tank. In further embodiments, the liquid polymer slurry is pushed through holes in a series of metal plates formed into a circle called a spinneret. The polymer slurry is pushed through a spinneret by applying pressure on the slurry. As the slurry is pushed through the fine holes that are close together, they form single fibers or if allowed to contact one another, they form a film or sheath. The hot liquid fiber or film is pushed upwards, cooled with cold air, forming a continuous series of fibers or a circular sheet. The thickness of the fibers or sheet is controlled by the size of the holes and speed at which the slurry is pushed through the holes and upward by the cooling air flow. In the preferred embodiments, the fibers are homogeneously extruded.

In some embodiments, step c. comprises forming a polymeric fiber from the mixture obtained in step b. The formation of a fiber can be in either filament form (continuous) or staple form (short cut). In both cases an amount of master batch is added to the hot polymeric slurry to yield the final amount of the combination of the at least two metal oxide powders desired for the end product. By way of example if a 1% final load is desired in a filament fiber than 50 kilo of a 20% wt. concentrated master batch will be added to complete 1 ton of total slurry. By way of example if a 3% final load is desired in a staple fiber than 150 kilo of a 20% wt. concentrated master batch will be added to complete 1 ton of total slurry. In both cases, after a thorough mixing of the concentrated master batch in the slurry tub to obtain good master batch dispersion, the extruded fibers will contain the desired amount of the metal oxides combination.

In a normal process as known to those familiar with the art, the active ingredient will be evenly dispersed and remain in suspension of the polymeric slurry. If the master batch is not prepared correctly then the metal oxides will interact with the target polymer and disrupt the linkage process thus inhibiting the formation of a solid fiber. In addition, if the wax is not applied correctly the metal oxides will either sink to the bottom of the mixing tub and block the holes of the spinneret or will remain floating at the top of the slurry and not get mixed into the fibers. Normally extrusion is done using gravity so that the weight of the slurry in the tub pushes the polymer through the spinneret holes. The polymer is designed to solidify with exposure to air. Once the fibers are exposed to air they are wound on bobbins for further processing.

According to some embodiments, the fiber is selected from the group consisting of a staple fiber, a filament fiber and a combination thereof. According to some embodiments, the polymer fiber is a synthetic or a semi-synthetic fiber. According to further embodiments, the synthetic or semi-synthetic fiber is selected from the group consisting of polyolefin fibers, polyurethane fibers, vinyl fibers, nylon fibers, polyester fibers, acrylic fibers, cellulose fibers, regenerated protein fibers, blends and combinations thereof. In some embodiments, the method further comprises blending the polymer fiber with a natural fiber. According to further embodiments, the natural fibers are selected from the group consisting of cotton, silk, wool, linen and combinations thereof.

According to further embodiments, the method includes forming the polymer fiber into a yarn. According to some embodiments, the yarn is a synthetic yarn or a combination of the synthetic yarn with a natural yarn. In some embodiments, the synthetic yarn is spun from said synthetic fibers. According to further embodiments, the yarn is formed into fabrics. According to further embodiments, the fabrics are woven, knit or non-woven.

In additional embodiments the method further comprises forming the material into a textile product or a non-textile polymeric article. According to further embodiments, step c. comprises directly forming from the mixture obtained in step b. a textile product or a non-textile polymeric article. Each possibility represents a separate embodiment of the invention. In certain such embodiments, step c includes molding, casting or extruding the mixture obtained in step b. into a desired shape or form. In certain embodiments, step c. comprises applying the mixture of the metal oxide powders with the at least one polymer, obtained in step b. to a pre-formed polymer article as a second layer. In some embodiments, the polymer is latex, nitrile or an artificial rubber.

The following examples are presented for illustrative purposes only and are to be construed as non-limitative to the scope of the invention.

EXAMPLES

Example 1: Mixed Oxidation State Oxide Powder Preparation

A tetrasilver tetroxide powder was prepared through a reduction process from a silver nitrate solution by a standard procedure known to a person skilled in the art, and as described by Hammer and Kleinberg in Inorganic Synthesis (volume IV, page 12). It should be further noted that the powder obtained by the described process should be very soft and capable of being converted into a nano-powder with a relative ease.

The basic tetrasilver tetroxide ($Ag_4O_4$) synthesis as referenced above was prepared by addition of NaOH into distilled water, followed by addition of a potassium persulfate and then the addition of silver nitrate.

A tetracopper tetroxide powder can be prepared using copper sulfate and potassium persulfate as an oxidizing agent, as described in U.S. Pat. No. 5,336,416 to Antelman. However, for the sake of commercial viability cuprous oxide was purchased and used as a starting material to obtain $Cu_4O_4$ according to the described procedure.

The particle size of both powders received varies from nano-particles to agglomerated particles as large as 20 microns.

These powders can be ground down to the desired particle size and mixed either together or with copper oxide or zinc oxide. The copper oxide used in the development is a cuprous oxide (brown/red) with a purity level of no less than 97% in a 10-20 μm size particle. In this case, the powder was purchased from SCM Inc. of North Carolina, USA, but can be purchased from any supplier who can furnish this purity level. The powder is then ground down to 1 to 5 μm. Due to the prevalence of suppliers of this powder it is not economically viable to manufacture the powder. However, due to the difficulty in obtaining tetrasilver tetroxide and/or tetracopper tetroxide, it is necessary to synthesize the specific species as described hereinabove.

Example 2: Master Batch Preparation

The metal oxides were incorporated into a polymer using a master batch system so that the powder is embedded on the outside of the polymer and forms part of the entire polymeric product.

To accommodate the different specific gravities of more than one metal oxide in a common master batch, it is necessary to compensate for the differences between the two different metals, should a difference in their weight exist. This is done using two systems as described:

In the first system, the particle sizes of each metal oxide were made equal through proportional size equalization. The specific gravity of copper oxide is approximately 6 g/ml and the specific gravity of tetrasilver tetroxide is 7.48 g/ml. Tetrasilver tetroxide particles were ground down to be approximately 10% to 15% smaller than the copper oxide particles.

In the second system, the particles were all ground to the same size but the heavier particles were coated with a higher amount of polyester wax or polyethylene wax.

The wax was applied in a high sheer mixer in a weight/weight ratio of approximately 10 grams wax to 1000 grams metal oxide. It was found that a higher amount of polyester wax on the heavier metal oxide aids in maintaining the suspension of the metal oxide in the polymer slurry. The wetting capability of the waxes should also be good. To isolate the metal oxide from a chemical interaction with the carrier polymer, the metal oxide powders were pretreated with an encapsulating compound. The inert encapsulating compounds used were a silicate and Poly(methyl methacrylate) (PMMA). The encapsulation was performed in a high sheer mixer in a weight/weight ratio of approximately 4 g encapsulating agent to 1000 g metal oxide powder.

Example 3: Polymer and Blended Polymer Fiber and Yarn Preparation

The fabrication of a polymeric yarn having antimicrobial properties, characterized by a protrusion of the metal oxide particles on the surface of the polymer in both a filament and staple product is described.

It should be noted that for the sake of this example, tetrasilver tetroxide and/or tetracopper tetroxide and/or copper oxide were used but that the proportions for using other metal oxides compounds are the same approximate proportions.

A description of the general production process of fibers is as follows:

1. Slurry is prepared from any polymer, the chief raw material preferably being selected from polyamide, polyalkene, polyurethane and polyester. Combinations of more than one of said materials can also be used provided they are compatible or adjusted for compatibility. The polymeric raw materials are usually in bead form and can be mono-component, bi-component or multi-component in nature. The beads are heated to melting at a temperature which preferably will range from about 120 to 180° C. for isotactic polymers and up to 270° C. for polyester.

2. At the hot mixing stage, before extrusion, a water insoluble powder of the chosen metal oxide compounds in the form of master batch is added to the slurry and allowed to spread through the heated slurry. The particulate size will be preferably between 1 and 5 microns, however particulate size can be larger when the film or fiber thickness can accommodate larger particles.

3. The liquid slurry is then pushed with pressure through holes in a series of metal plates formed into a circle called a spinneret. As the slurry is pushed through the fine holes that are close together, they form single fibers or if allowed to contact one another, they form a film or sheath. The hot liquid fiber or film is pushed upwards, cooled with cold air, forming a continuous series of fibers or a circular sheet. The thickness of the fibers or sheet is controlled by the size of the holes and speed at which the slurry is pushed through the holes and upward by the cooling air flow.

Filament Fiber

It is noted that the specific gravity of each metal oxide is different and therefore required a treatment of a different coating compound or applying different amount of the same coating compound so that both metal oxide powders would be homogeneously dispersed in the liquid polyester slurry. The metal oxide particles were mixed with the carrier and formed into pellets. As it relates to filament fiber this produces a total of 50 kilo of master batch which is a total of the copper oxide and/or the tetrasilver and/or tetracopper tetroxide is together. The proportion of the carrier to active material was 5:1 yielding a 20% wt. concentration of the metal oxides in the master batch. 50 kilo of the master batch were mixed into an extrusion tank for spinning through a spinneret and were sufficient to produce 1 ton of a filament polymeric yarn yielding a total of a 1% final concentration of the two metal oxides (active material) together in the polymer yarn. It should be noted that if the particles are below 0.5 microns in size it was found that the loading of the metal oxides in a filament fiber can be increased to as much as 4% wt.

Staple Fiber

For the production of a staple fiber, 28.5 kilo of copper oxide having particle size ground to 1 to 5 microns and 1.5 kilo of tetrasilver tetroxide ground to 1 to 5 microns were mixed with 120 kilo of the chosen carrier polyester polymer for the creation of a master batch. The specific gravity of each compound was different and therefore required a coating by a different coating compound, such as Clariant Licowax PP230 and BASF Luwax® or by different amounts of said compounds, such that the metal oxide particles would be homogeneously dispersed in the suspension. The compounds were mixed with the carrier and were formed into pellets. This produced a total of 150 kilo of master batch. The 150 kilo of master batch was mixed into an extrusion tank for spinning through a spinneret and was sufficient to produce 1 ton of a polymeric staple yarn yielding a total of a 3% wt. final concentration of the two compounds in the polymer fiber.

Figure 1B:
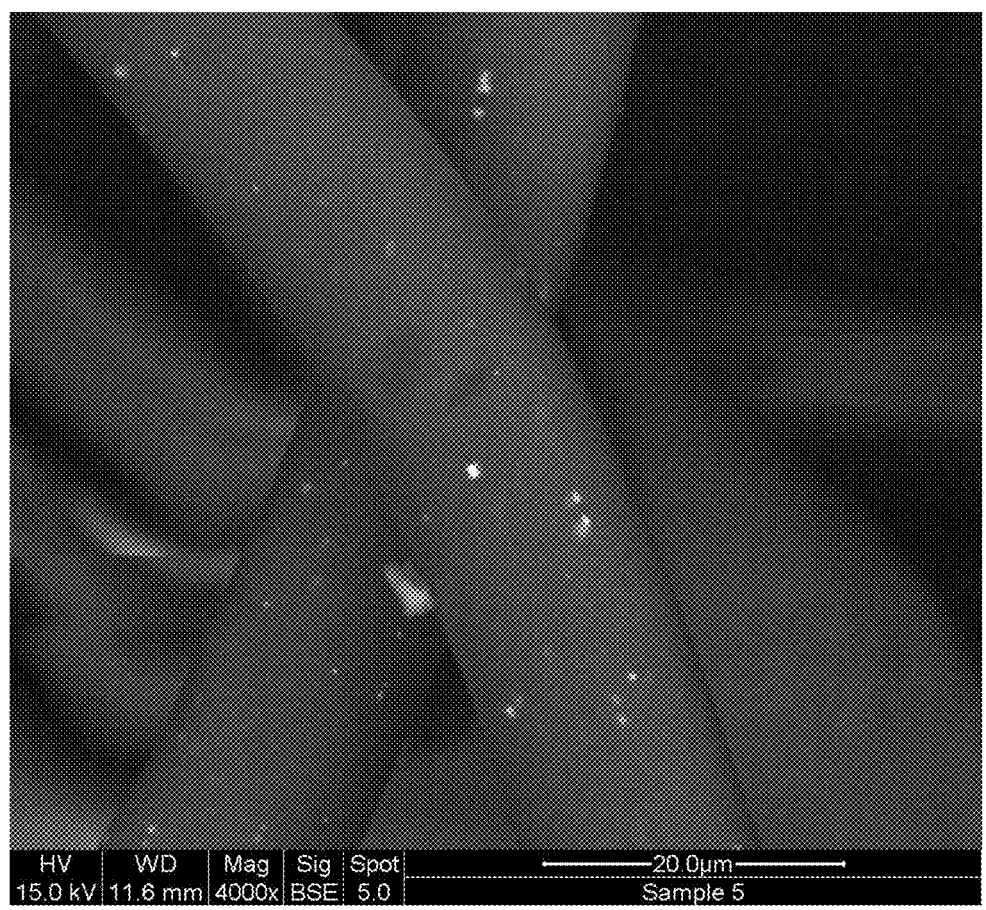
FIG. 1B: SEM micrograph of a polyester staple fiber containing copper oxide and tetrasilver tetroxide, prepared by a master batch preparation method, at 4000× magnification with protruding particles.
Figure 1C:
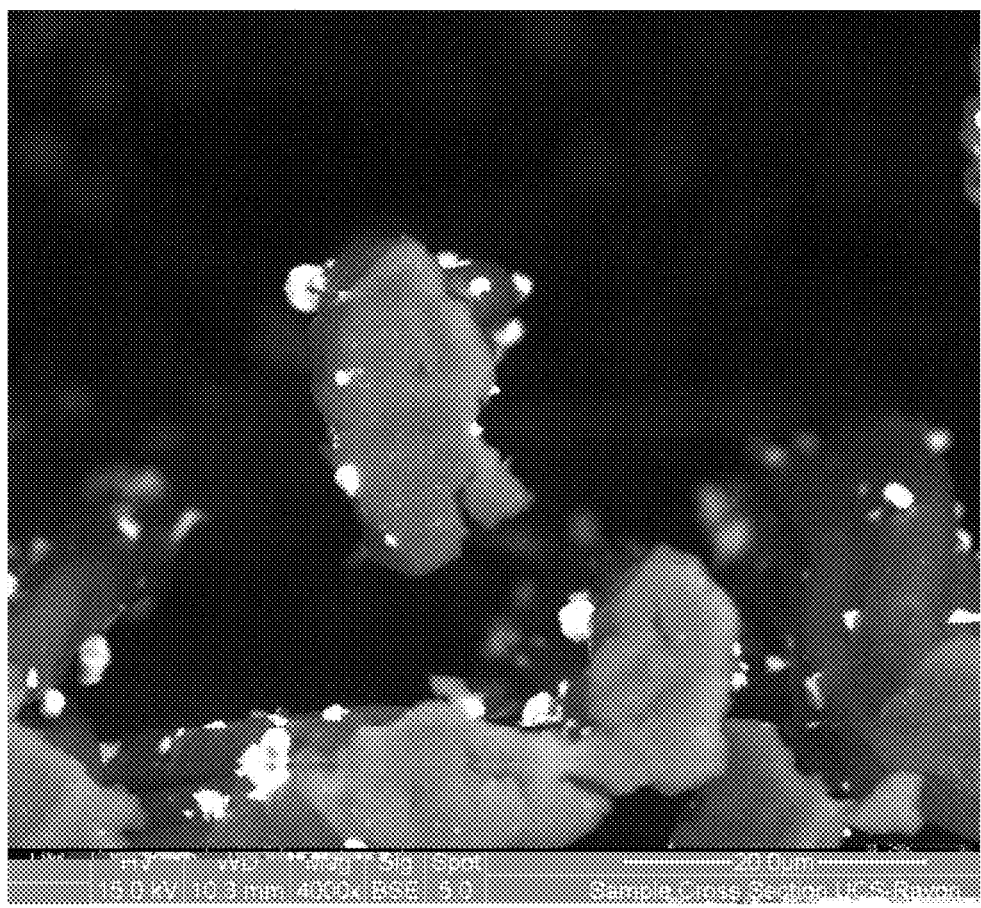
FIG. 1C: SEM micrograph of a cross section of the fiber of FIG. 1A and FIG. 1B, showing copper oxide and tetrasilver tetroxide at 4000× magnification with protruding particles.

FIGS. 1A-1C present Scanning Electron Microscope (SEM) micrographs of a polyester staple fiber having a combination of copper oxide and tetrasilver tetroxide powders incorporated within. The polymer fiber was prepared by a master batch process as described hereinabove. It can be seen that the metal oxide particles are uniformly distributed on the surface of the polymer fiber. It can also be seen that the metal oxide particles of the synergistic combination protrude from the surface of said polymer fiber.

Figure 2A:
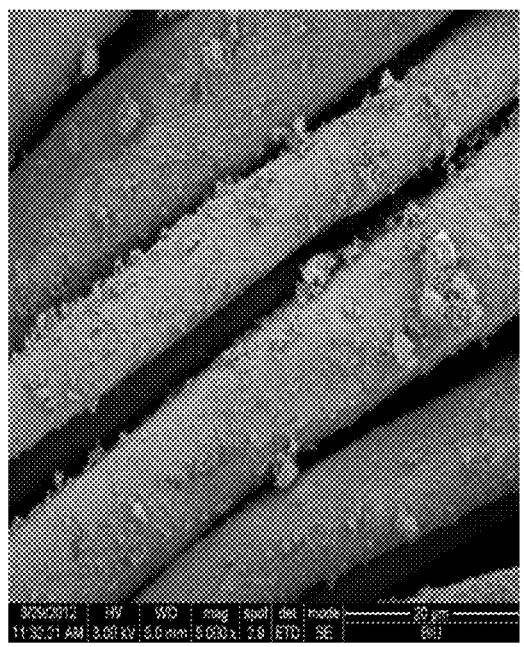
FIG. 2A: SEM micrograph of a cotton fiber with sonochemically nano-deposited copper oxide impregnated with tetrasilver tetroxide at 5000× magnification.
Figure 2B:
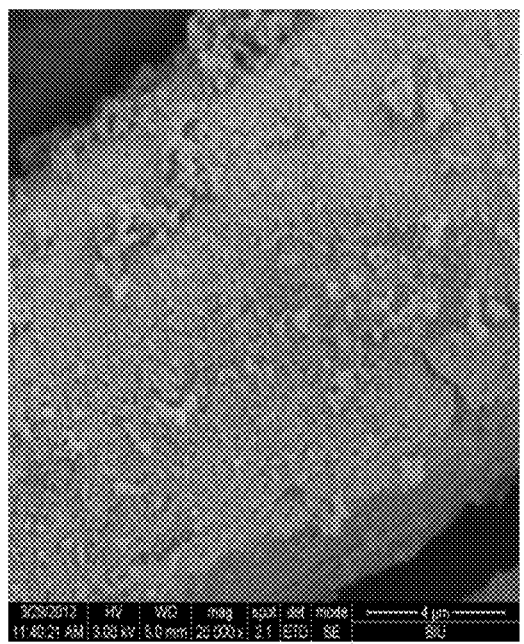
FIG. 2B: SEM micrograph of a cotton fiber with sonochemically nano-deposited copper oxide impregnated with tetrasilver tetroxide at 20000× magnification.

As a comparative study, FIG. 2A and FIG. 2B represent a cotton fiber comprising sonochemically deposited copper oxide and further impregnated with tetrasilver tetroxide. The larger particles are tetrasilver tetroxide particles and the smaller particles are copper oxide particles.

It has been further found that the load level in a polyolefin fiber can be much higher than in a polyester or nylon fiber due to the isotactic nature of the olefins. While load levels as discussed above were limited to 1% wt. in filament fibers and 3% wt. in staple fibers, it was found that as much as 20% wt. could be added to polypropylene fibers.

Staple and Filament Fiber Combined with Cotton.

A master batch was created as described hereinabove, using polyester resins to which 20 wt. of a mixture comprising copper oxide and TST was added. Both the copper oxide and the TST were about 98% pure. The metal oxide composition comprised 99.5% copper oxide and 0.5% wt. TST. The master batch was then added to a polyester slurry being in a liquid form in a proportion that yielded a final loading of copper oxide of about 3% wt. in the final fiber. The copper oxide in the sample was 97.7% pure with 2.3% being impurities. The fibers were extruded in the same manner as normal staple polyester fibers and were then blended with cotton so that the final load of treated fibers is a total of 30% wt. copper oxide and TST impregnated fibers/70% cotton in a 24/is forming a ring spun combed cotton yarn twisted for weaving. The yarns were then knit into a fabric that weighs 150 grams to the square meter.

It should be noted that in the mixtures comprising up to 10% by weight of the metal oxide, no degradation of the physical properties was observed. As described hereinbelow, the materials having as low as 0.5% wt. of the metal oxides combination demonstrated limited efficacy in antimicrobial properties, as well as surprising inhibition of HIV-1 activity.

Example 4: Preparation of Staple Fiber Having Encapsulated Metal Oxide Powders

A polyester staple fiber was prepared by combining copper oxide powder which constituted 2.85% wt. of the total weight of the fiber and tetrasilver tetroxide powder which constituted 0.015% wt. of the total weigh of the fiber. The particle size of the metal oxides was brought down to between 0.25 to 0.35 microns and the powders were incorporated directly into the polymer fiber. The process included milling the powders to the desired size, placing the powders on the fiber and passing the fiber with the powders through a trough of water though which ultrasonic waves were passed.

Figure 3:
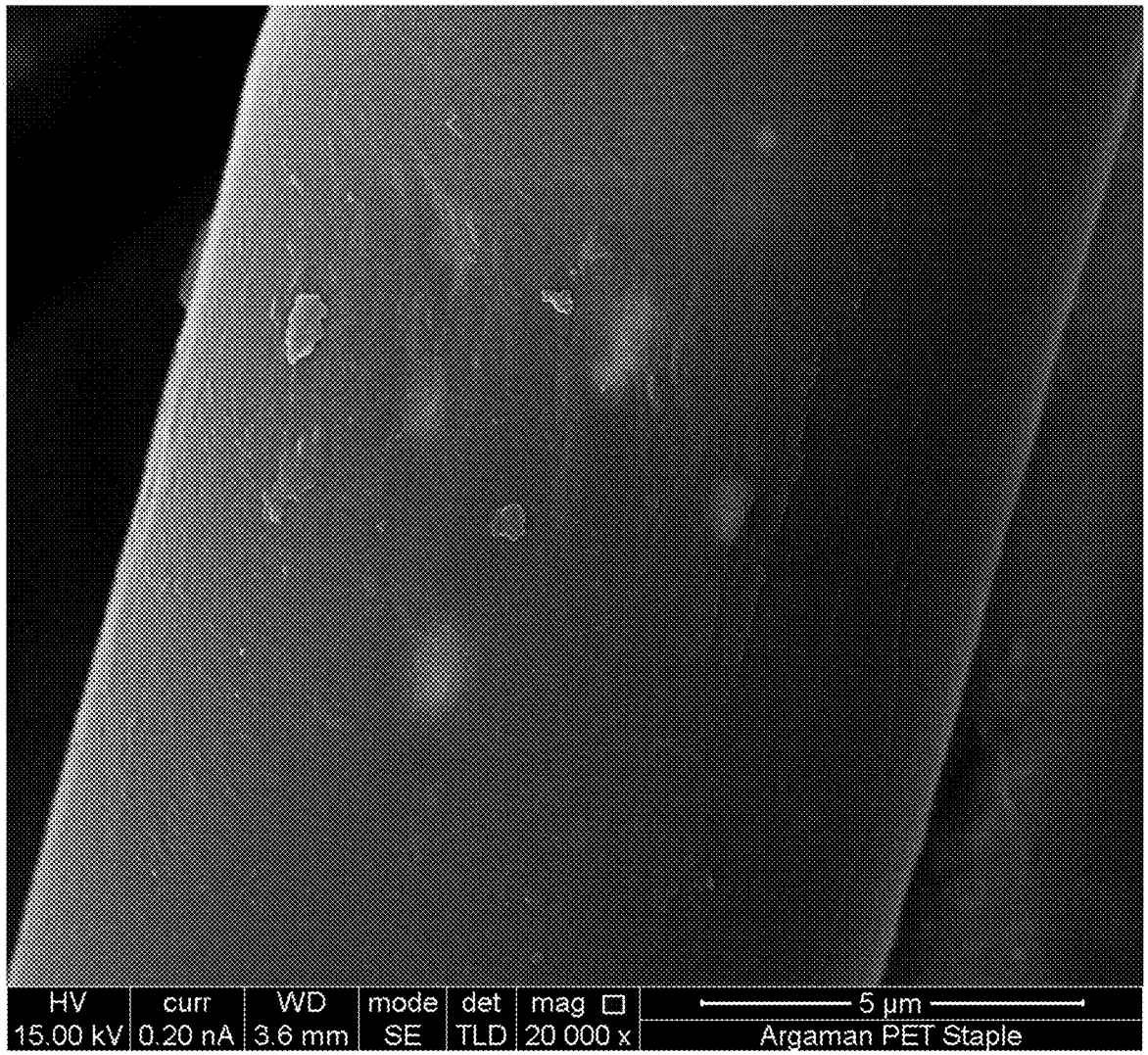
FIG. 3: SEM micrograph of a polyester staple fiber impregnated with copper oxide and tetrasilver tetroxide, via a sonication assisted process, at 20000× magnification with particles enclosed within the fiber.

FIG. 3 shows SEM micrograph of the fibers obtained via said process, wherein the copper oxide and TST particles are under the surface which appear as unclear white spots in the SEM micrograph. Particles on the fibers surface in the photographs were evaluated by a spectrographic reading and found not to be copper oxide or TST but rather a combination of complex organic groups which are the polymer itself.

Example 5: Polymer Yarn Preparation Through a Standard Extrusion Process

The same procedure as in Example 3 was followed for the preparation of the master batch but the yarn was obtained through a procedure involving standard film extrusion equipment. The viscosity of the slurry was controlled through the master batch flow rates, by a procedure which is known to those familiar with the art.

Example 6: Molded Polymer Preparation

The powders and the master batch including the combined powders including copper oxide and TST, and polypropylene were prepared as described hereinabove. The master batch has to accommodate the carrier polymeric slurry into which it will be added. In molded and/or cast products the master batch concentration can be any amount up to and including 40% active ingredient however, amounts of 20% to 25% would be preferred so as to avoid possible problems in the chemical dispersion in the slurry. The master batch was allowed to melt in the polymeric slurry until the slurry was homogenous. No temperature changes were made. The polymeric slurry is then cast into a desired form or extruded to produce a product of a particular shape. The polypropylene slurry was extruded into a polypropylene film having copper oxide and TST incorporated therein.

Example 7: Cellulose-Based Polymer Yarn Preparation

A rayon slurry or any cellulose slurry (waste of cotton and corn are very popular as a source of cellulose) is mixed with a plasticizer as is known in the industry of the production of these types of fibers. Normally the process involves a number of chemical steps that involve the breaking down of cellulose to very fine mulch of individual cells, adding a plasticizer, and then exposing the slurry to a solidifying process.

A powder made up of a combination of the two metal oxides, including copper oxide and tetrasilver tetroxide, was prepared. The metal powders were thoroughly mixed together and ground down to a particulate size of preferably under 5 μm.

The powder was then added to the cellulose based slurry in a ratio of up to 3% wt. of the powder to the total weight of the slurry. The powder was added exactly at the same time the slurry is being passed through the holes of the spinneret so that the exposure to the acid in the final step of the process is limited to a few seconds as is common in the way these fibers are made.

The resulting slurry was solidified such that the metal oxide particles are homogeneously impregnated throughout the fiber.

Example 8: Latex Glove Preparation

A natural latex slurry is prepared using the accepted amount of latex solids and water and other compounds. In the case of a glove there is usually between 20% and 35% latex solids. The slurry is heated and a glove mold is dipped into the liquid and removed. The excess latex is allowed to drip off the glove which is still on the mold, thus creating a thin layer of latex on the mold. The latex and mold are then placed in an oven which cures the latex at the temperatures needed to cause the cross linking of the material. This first curing of the latex converts the liquid latex to a latex solid. The latex layer is allowed to cool but will remain sticky until it is dried through a second exposure to dry heat. After the first curing the latex is cross linked and now has the form of a flexible film in molded form but is still in a sticky state.

While the latex on the mold is still sticky but solid, and before the second exposure to heat, a second bath is prepared. The mold and the sticky latex are dipped in a latex slurry for a second time. The second bath is also a latex slurry but contains as much as but not limited to 5% wt. latex solids and 0.25% wt. of a copper oxide and TST mixture. This amount of copper oxide and TST was found to be sufficient for the antimicrobial and antiviral effect. When the sticky molded glove was dipped in the diluted latex copper oxide and TST bath a very thin colored coating was created which could be seen on the glove. At this stage it was also found that a pigment could be added to the slurry to change the color of the glove if so desired.

The particle size of the copper oxide and the TST in the system was measured to be approximately 5 μm but this procedure can be performed with both smaller and larger particles. Preferably, the copper oxide particles protrude from the surface of the latex.

It should be noted that the second latex dip acts only as a binder to the copper oxide, and binds excellently to the latex below the layer, allowing for the exposed copper oxide and TST mixture to be bound to the latex without any negative weakening of the latex glove. The mold with the two layers of latex is cured a second time and is run through a drying process. There was no need for another curing of the outer layer due to its low thickness.

Example 9: Antimicrobial Properties of the Metal Oxides

This example contains several experiments performed to test the antimicrobial properties of the combination of the single oxidation state and mixed oxidation state oxides.

Test 1: Antiviral Properties

100 μl aliquots of freshly prepared HIV-1 were incubated on top of the fibers produced according to the procedure described in Example 3, with varying amounts and ratios of copper oxide and tetrasilver tetroxide, as presented in Table 1. The incubation was performed for 30 minutes at 37° C. Then 10 μl of each incubated virus solution were added to MT-2 cells (human lymphocyte cell line) cultured in 1 ml neutral medium. The cells were then incubated for 5 days in a moist incubator at 37° C. and the virus proliferation was determined by measuring the amount of p24 (HIV-1 capsid protein) in the supernatant with a commercial ELISA (enzyme linked immunesorbent assay) kit. The results show the average of duplicate experiments. As control for possible cytotoxicity of the $Ag_4O_4$ in combination with copper oxide to the cells, similar experiments were carried out as above. The fibers were incubated with 100 μl of standard/control medium that did not contain HIV-1. No cytotoxicity was observed.

Table 1 summarizes the evaluation of the ability of the fibers containing a combination of $Ag_4O_4$ and copper oxide, to inhibit HIV-1 proliferation in tissue culture, as compared to the fibers, containing copper oxide or tetrasilver tetroxide alone and to fibers, which do not contain metal oxides.

TABLE 1

Anti-viral efficacy test results.

| Test # | Polymeric Fiber active material | Inhibition (%) |
| --- | --- | --- |
| 1 | Control - no anti-viral agent | 0 |
| 2 | With 1% wt. $Cu_2O$ | 70 |
| 3 | With 1% wt. TST | 76 |
| 4 | With 0.1% wt. TST/1% wt. $Cu_2O$ | 96 |

Test 2: Anti-Bacterial, Anti-Fungal and Anti-Mite Properties.

Extruded polypropylene films containing a combination of copper oxide and TST were used to test antibacterial properties of the extruded polymer comprising a synergistic combination of the metal oxides. The films were prepared as described in Example 5. In all cases, the mixed oxidation state oxide—tetrasilver tetroxide and the single oxidation state oxide—copper oxide together constituted 3% wt. of the total weight of the extruded film. The mixture of the metal oxides comprised 3% wt. TST and 97% wt. copper oxide. As a control, a polypropylene film containing a single oxidation state oxide as a sole active ingredient was tested so that levels of microbial inhibition could be observed. As a control for combined metal oxides activity, a polypropylene film was extruded with a copper oxide and an elemental silver ceramic compound typically used as a silver-based antimicrobial material, thus providing a polymer having a combination of two single oxidation state oxides. The combined weight of copper oxide and the silver ceramic compound powders constituted 3% wt. of the total weight of the extruded film. The combined powders comprised 3% wt.

silver (AlphaSan® silver based antimicrobial additive from Milliken, Inc. of the USA) and 97% copper oxide.

Polymer fibers combined with cotton, containing a combination of copper oxide and TST were used to test dust-mites biocidal properties of the fibers comprising a synergistic combination of the metal oxides. The polymer/cotton blend fibers were prepared as described in Example 3. The metal oxide composition comprised 99.5% copper oxide and 0.5% wt. TST. The blended fibers included 30% wt. copper oxide and TST impregnated fibers and 70% cotton. As a control, a 70% polymer/30% cotton blend fibers containing a single oxidation state oxide as a sole active ingredient were used. The positive control was made exactly as the combination copper oxide and TST but without the TST so that the active ingredient was 100% copper oxide. The negative control was again made the same as the two other fibers but with no active ingredient.

The American Association of Textile Chemists and Colorist (AATCC) Test Method 100 was used to determine the biocidal properties of the films against the bacteria and fungi tested. The initial bacterial or fungal inoculum used varied between $1 \times 10^5$ and $4 \times 10^6$ colony forming units (CFU) per ml. However, in an attempt to see the pure effect of the metal oxides, the sample film used in these tests which contained the bacteria were diluted using a saline solution so that growth medium was highly diluted and removed from the films and bacterial proliferation was significantly reduced when incubated at 25° C. and 70% relative humidity.

Measurements of the micro-organism levels were performed at 5 minute intervals for biocidal activity evaluation of every film towards each of the micro-organisms. The time recorded below relates to the time required to achieve a kill rate, which provides a 99% reduction (a 2-log reduction) in the micro-organism levels.

Figure 4:
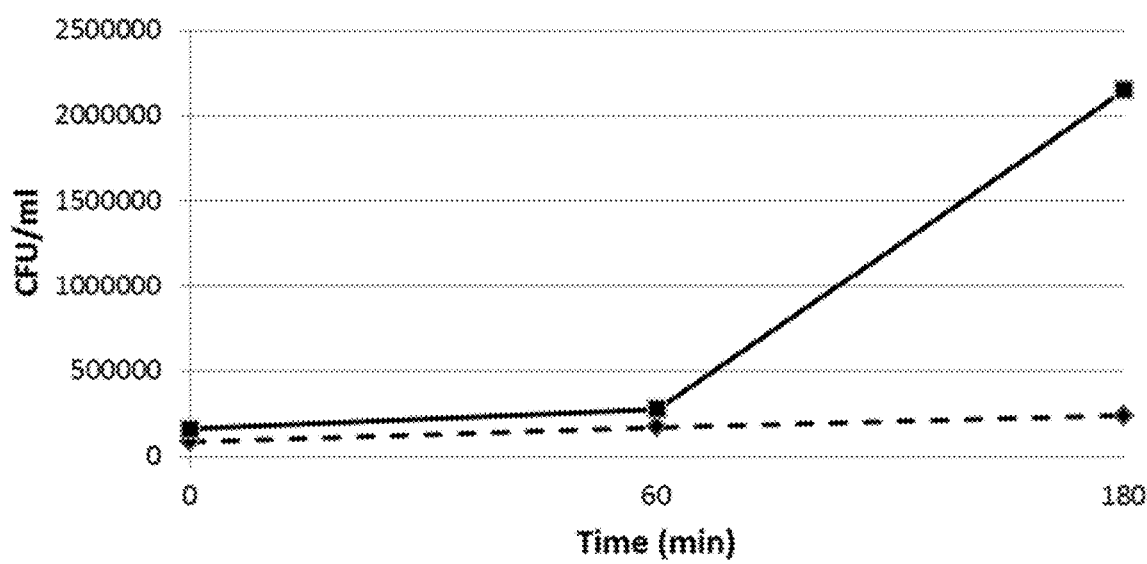
FIG. 4: Bacteria proliferation inhibition of the extruded polypropylene film comprising copper oxide and tetrasilver tetroxide (dashed line) as compared to the control (solid line), which is untreated polypropylene film of the same material and size.
Figure 5A:
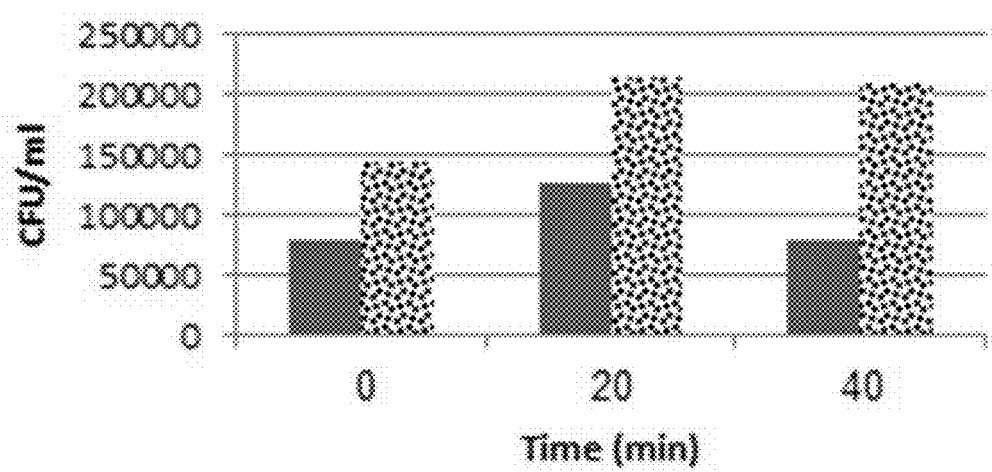
FIGS. 5A-5C: Bacteria proliferation inhibition of the polymeric fabric comprising copper oxide and tetrasilver tetroxide, wherein solid color bars represent a polymeric fabric comprising a combination of copper oxide and TST, and confetti pattern bars represent control—untreated fabric of the same material and size.
Figure 5B:
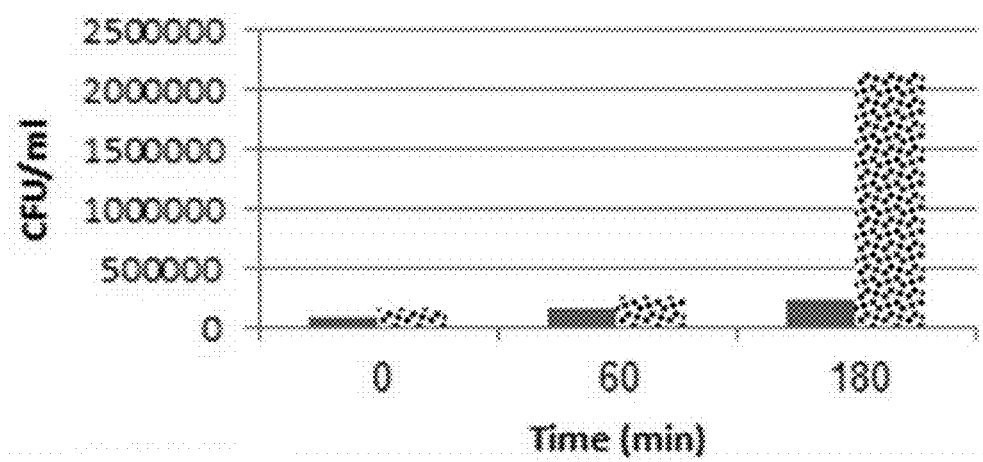
Figure 5C:
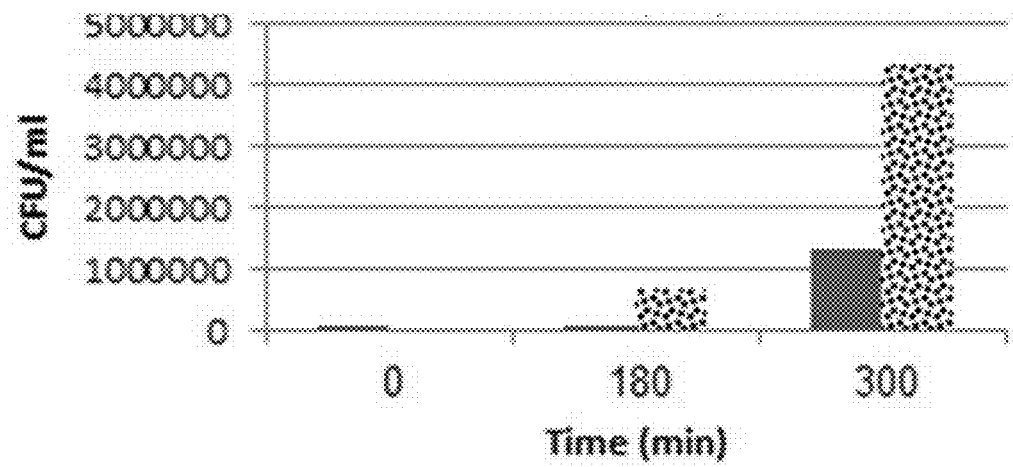
Figure 6A:
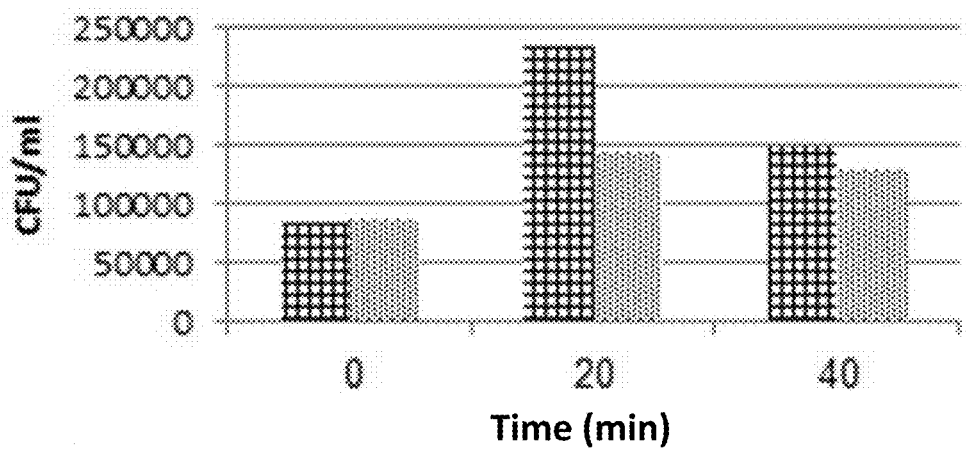
FIGS. 6A-6B: Bacteria proliferation inhibition of the polymeric fabric comprising copper oxide, wherein grid pattern bars represent a polymeric fabric comprising copper oxide, and dotted pattern bars represent control—untreated fabric of the same material and size.
Figure 6B:
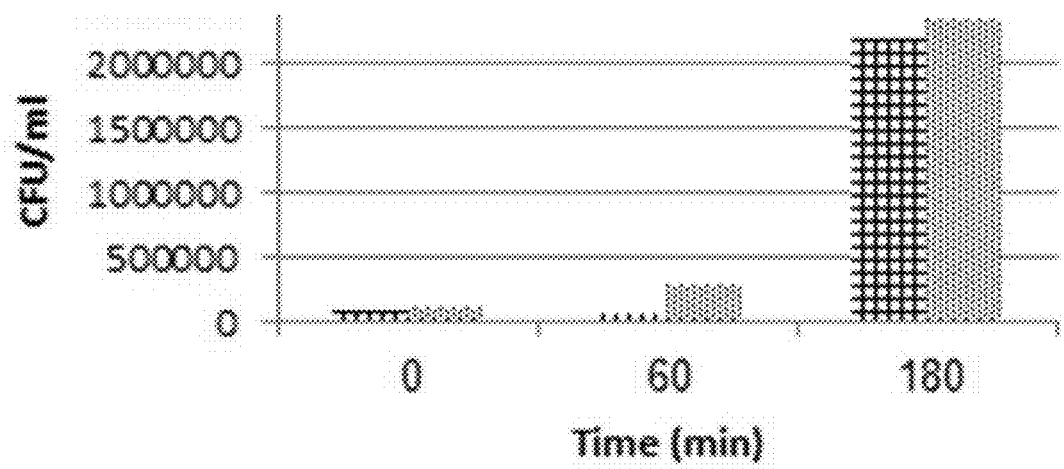

The tested antibacterial properties of the material, which includes a combination of two single oxidation state oxides instead of a combination of a mixed oxidation state oxide and a single oxidation state oxide, as compared to such properties of a single oxidation state oxide alone, are presented in Table 2. The tested antibacterial, antiviral and anti-mite properties of the materials comprising a combination of a mixed oxidation state oxide and a single oxidation state oxide, as compared to such properties of a single oxidation state oxide alone, are presented in Table 3. The tested antibacterial properties of the polypropylene extruded film, which includes a combination of copper oxide and TST, as compared to a control, which is the same fiber without any active ingredient, are presented in FIG. 4.

Other than the final test in Table 3 (dust mites), times were measured at 5 minute intervals until the 99% reduction in the micro-organism levels was reached. All tests were done in triplicates and the results in the table represent an average. In the final test (dust mites on 70% cotton, 30% polyester), times were measured at 24 hour intervals until the 99% reduction in the micro-organism levels was reached.

As can be seen from Table 2, addition of AlphaSan® to copper oxide did not reduce the time required for a 2-log reduction by the polypropylene film containing AlphaSan® and copper oxide. In contrast, Table 3 shows that polymer films and fibers including a combination of tetrasilver tetroxide (silver in the form of mixed oxidation state) and copper oxide had higher biocidal activity that films and fibers containing copper oxide alone, as expressed by shorter times required to achieve the 2-log reduction.

TABLE 2

Antibacterial properties of the polumeric material, which includes a combination of two single oxidation state oxides.

| | $Cu_2O$ | | $Cu_2O$/AlphaSan ® | |
|---|---|---|---|---|
| Micro-organism tested | Time [min] | Reduction [%] | Time [min] | Reduction [%] |
| S. aureus (Gram+) (Staphylococcus) | 60 | 99.8 | 60 | 99.7 |
| E. coli (Gram−) | 55 | 99.5 | 60 | 99.6 |

TABLE 3

Antibacterial, antiviral and anti-mite properties of the materials comprising a combination of a mixed oxidation state oxide and a single oxidation state oxide.

| | | $Cu_2O$ | | $Cu_2O$/TST | |
|---|---|---|---|---|---|
| | Organism Tested | Time | Reduction [%] | Time | Reduction [%] |
| Polymeric Material | S. aureus | 60 Min. | 99.8 | 15 Min. | 99.7 |
| | E. coli | 55 Min. | 99.5 | 15 Min. | 99.6 |
| | C. albicans (Candida) | 120 Min. | 99.9 | 25 Min. | 99.5 |
| | L. monocytogenes, Gram+ (Listeria) | 60 Min. | 99.8 | 15 Min. | 99.3 |
| | S. enterica, Gram− (Salmonella) | 110 Min. | 99.0 | 25 Min. | 99.2 |
| 70% Cotton/ 30% Polyester Fabric | Dust mites * (Dermatophagoides) | 5 days | 100 | 3 days | 100 |

* 100 Dust Mites were placed on the film with food and placed in an incubator at 37° C. at 70% relative humidity. Mortality rates were counted once a day.

Example 10: Proliferation Inhibition Testing on Polymer Fabrics Using AATCC Test Method 100-2004

The previous set of experiments (Example 9) simulated a scenario where bacteria reside on a film which is not being worn by a person. Hence, the experimental conditions were set up to follow such scenario (incubation with no added nutrients, at room temperature).

The current experiment deals with a more realistic situation in which the fabric is worn in close proximity by a person. The human body acts as a reservoir and constantly supplies moisture, heat, and nutrients to microorganisms residing on the fabric via perspiration. Therefore, the incubation of bacteria on the fabric was carried out in 37° C. and with nutrients, as per AATCC Test Method 100-2004.

Two types of samples were prepared. One type (regular copper oxide fabrics) included fabrics containing 3% wt. copper oxide in a polyester fiber. Another type (accelerated copper oxide fabrics) contained 2.4% wt. copper oxide+ TST, of which copper oxide constituted 99.5% wt. and TST constituted 0.5% wt. in the same size polyester fiber as the fiber above.

All fabrics were sterilized prior to use via submergence in ethanol 70% for 10 minutes, followed by overnight drying in a sterile environment. Bacteria (*E. coli*) were grown overnight in a LB medium (10% tryptone 5% yeast extract, 10% NaCl (wt. %)) and diluted to approximately $10^5$ CFU/ml with a fresh autoclaved LB medium. The treated fabrics and the controls were then soaked with 1 ml of the bacteria containing medium, placed in a closed sterile jar and incubated at 37° C. for the specified times.

Bacteria were extracted from the fabrics using fresh LB medium and then 200 µl were seeded on LB-agar petri dishes overnight to allow the growth of colonies.

The effective reduction of the population of bacteria on each fabric was compared to its own control untreated fabric of the same material weave and size. Each experiment was done in duplicate, and averaged. The test results are presented in Tables 4-6.

TABLE 4

Effective reduction of the population of bacteria by applying fabrics comprising a single oxidation state oxide or a combination of a mixed oxidation state oxide and a single oxidation state oxide measured at the time period of 0-40 min

| Time | Copper oxide + TST | | | Copper oxide | | |
|---|---|---|---|---|---|---|
| (min) | Treated | Untreated | Reduction | Treated | Untreated | Reduction |
| 0 | 80,000 | 145,000 | 44.82% | 85,000 | 87,500 | NR |
| 20 | 127,500 | 215,000 | 40.69% | 235,000 | 145,000 | −62.01% |
| 40 | 80,000 | 210,000 | 61.90% | 150,000 | 130,000 | −15.38% |

TABLE 5

Effective reduction of the population of bacteria by applying fabrics comprising a single oxidation state oxide or a combination of a mixed oxidation state oxide and a single oxidation state oxide measured at the time period of 0-180 min

| Time | Copper oxide + TST | | | Copper oxide | | |
|---|---|---|---|---|---|---|
| (min) | Treated | Untreated | Reduction | Treated | Untreated | Reduction |
| 0 | 87,500 | 162,500 | 46.15% | 107,500 | 122,500 | NR |
| 60 | 172,500 | 280,000 | 38.39% | 82,500 | 307,500 | 73.17% |
| 180 | 240,000 | 2,150,000 | 88.83% | 2,200,000 | 2,347,500 | 6.28% |

TABLE 6

Effective reduction of the population of bacteria by applying fabrics comprising a combination of a mixed oxidation state oxide and a single oxidation state oxide measured at the time period of 0-300 min
Copper oxide + TST

| Time (min) | Treated | Untreated | Reduction |
|---|---|---|---|
| 0 | 82,500 | 60,000 | NR |
| 180 | 87,500 | 632,500 | 86.16% |
| 300 | 1,335,000 | 4,300,000 | 68.95% |

The bacteria proliferation inhibiting properties of the tested fabrics are also presented in FIGS. 5A-5C and FIGS. 6A-6B.

The results show that the fabric treated with copper oxide and TST is more effective in inhibition of bacterial growth as compared to copper oxide alone, especially in the longer timescales of higher than 180 min.

Example 11: Proliferation Inhibition Testing on Blended Polymer-Cotton Fabrics Using AATCC Test Method 100-2004

Two types of samples were prepared. One type (regular copper oxide fabrics) included a combination of polyester and cotton fibers, wherein the polymer fiber contained 3% wt. copper oxide relatively to the total weight of the polymer fiber. The copper oxide in the sample was 97.7% pure with 2.3% being impurities. The fibers were extruded in the same manner as normal staple polyester fibers and were then blended with cotton so that the final load of treated fibers is 30% copper oxide impregnated fibers/70% cotton in a 24/ls forming a ring spun combed cotton yarn twisted for weaving. The yarns were then knit into a fabric that weighs 150 grams to the square meter.

Another type (accelerated copper oxide fabrics) included a combination of polyester and cotton fibers, wherein the polymer fiber is impregnated with 3% wt. copper oxide+ TST, of which copper oxide constituted 99.5% wt. and TST constituted 0.5% wt. The fibers were extruded in the same manner as normal staple polyester fibers and were then blended with cotton so that the final load of treated fibers is a total of 30% copper oxide and TST accelerator impregnated fibers/70% cotton in a 24/ls forming a ring spun combed cotton yarn twisted for weaving. The yarns were then knit into a fabric that weighs 150 grams to the square meter.

The two types of samples were tested using AATCC Test Method 100-2004 (Quantitative), as described in Example 10, against a control fabric. The control comprised 30% untreated polyester/70% cotton fabrics with a weight of approximately 150 grams to the square meter. No fabrics were dyed. All fabrics were sterilized prior to use via submergence in ethanol 70% for 10 minutes, followed by overnight drying in a sterile environment.

Figure 7:
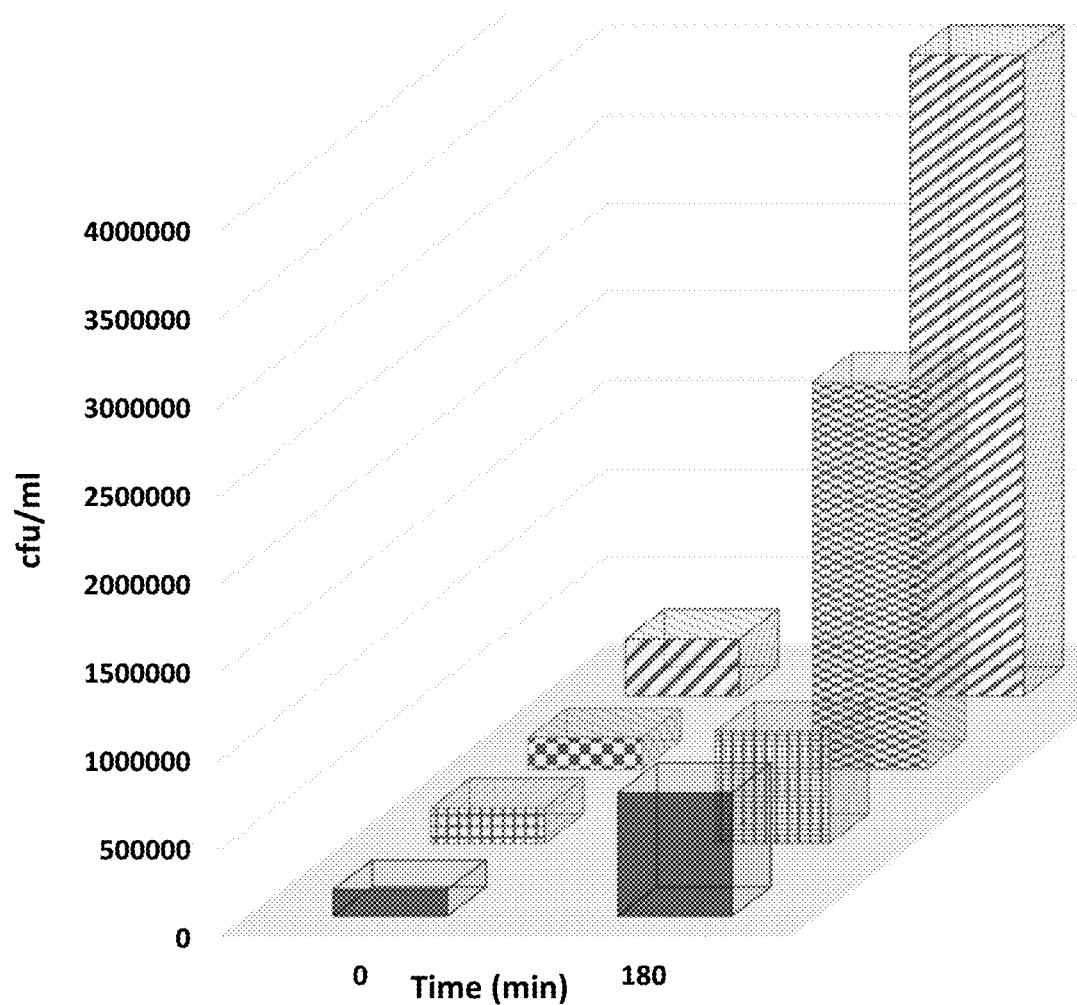
FIG. 7: Bacteria proliferation inhibition of the cotton blend polymeric fabrics comprising copper oxide and tetrasilver tetroxide and copper oxide alone, wherein stripes patter bars represent an untreated control (70% cotton/30% polyester fiber), checker board pattern bars represent 70% cotton/30% polyester fiber containing copper oxide, grid pattern bars represent 50% cotton/50% polyester fiber containing a combination of copper oxide and TST, and solid color bars represent 70% cotton/30% polyester fiber containing a combination of copper oxide and TST.

The results of the bacterial proliferation inhibition test are presented in FIG. 7. It was clearly shown that the polymer-cotton blend fabrics comprising a combination of a mixed oxidation state oxide and a single oxidation state oxide have higher antimicrobial activity as compared to the same fabrics comprising single oxidation state oxide alone.

Example 12: Detection of the Mixed Oxidation State Oxide in the Polymer Material A portion of textiles or fibers or molded or cast product is put in an oven and brought to a temperature which allows the polymer to be carbonized to dust, but which is below the melting temperature of the metal oxides. The dust is then placed in an X-Ray Diffraction system which identifies crystalline structure of a crystal and as such can detect the presence of the metal oxides powders in the sample, which are present in addition to the carbon dust.

While the present invention has been particularly described, persons skilled in the art will appreciate that many variations and modifications can be made. Therefore, the invention is not to be construed as restricted to the particularly described embodiments, rather the scope, spirit and concept of the invention will be more readily understood by reference to the claims which follow.

The invention claimed is:

1. A material having antimicrobial properties, said material comprising a synergistic combination of at least two metal oxide powders, comprising a mixed oxidation state oxide of a first metal and a single oxidation state oxide of a second metal, wherein the mixed oxidation state oxide constitutes from about 0.05% to about 15% wt. of the total weight of the synergistic combination of the at least two metal oxide powders and wherein the ions of the metal oxides are in ionic contact upon exposure of said material to moisture.

2. The material according to claim 1, wherein the mixed oxidation state oxide is selected from the group consisting of tetrasilver tetroxide ($Ag_4O_4$), $Ag_2O_2$, tetracopper tetroxide ($Cu_4O_4$), Cu (I,III) oxide, Cu (II,III) oxide and combinations thereof.

3. The material according to claim 1, wherein the single oxidation state oxide is selected from the group consisting of copper oxide, silver oxide, zinc oxide and combinations thereof.

4. The material according to claim 1, wherein the synergistic combination of the at least two metal oxide powders comprises copper oxide and tetrasilver tetroxide.

5. The material according to claim 1, wherein the mixed oxidation state oxide constitutes from about 0.5% to about 5% of the total weight of the synergistic combination of the at least two metal oxide powders.

6. The material according to claim 1, wherein each of the metal oxide powders independently comprises particles, which size is from about 10 nanometers to about 10 microns.

7. The material according to claim 1, wherein the metal oxide powders comprise particles encapsulated within an encapsulating compound.

8. The material according to claim 7, wherein the encapsulating compound is selected from the group consisting of silicates, acrylates, cellulose, protein-based compounds, peptide-based compounds, derivatives and combinations thereof.

9. The material according to claim 7, wherein the weight of the encapsulating compound applied to the powder constitutes from about 0.2% to about 2% wt. of the metal oxide powder weight.

10. The material according to claim 1, being in a form of a product selected from the group consisting of pillowcases, eye-masks, gloves, socks, stockings, sleeves, shoe covers, slippers, undergarments, uniforms, sportswear, towels, kitchen cloths, lab coats, floor cloths, bedding, curtains, diapers, incontinence pads, feminine hygiene products, gauze pads, trans-dermal patches, bandages, adhesive bandages, sutures, textiles for internal use, and absorbent pads.

11. A method of combating the activity of microbes or micro-organisms, selected from the group consisting of gram-positive bacteria, gram-negative bacteria, fungi, parasites, mold, spores, yeasts, protozoa, algae, acarii and viruses, the method comprising providing to health care facilities the material according to claim 1.

* * * * *